US012784908B2

(12) United States Patent
Manakkil et al.

(10) Patent No.: US 12,784,908 B2
(45) **Date of Patent: *Nov. 3, 2026**

(54) SECURE ARTIFICIAL INTELLIGENCE ENABLED MEDICAL SENSOR PLATFORMS

(71) Applicant: Fresenius Medical Care Holdings, Inc., Waltham, MA (US)

(72) Inventors: Joseph Edwin Inase Manakkil, San Ramon, CA (US); Norbert Leinfellner, Livermore, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 193 days.

This patent is subject to a terminal disclaimer.

(21) Appl. No.: 18/351,659

(22) Filed: Jul. 13, 2023

(65) Prior Publication Data

US 2023/0360789 A1 Nov. 9, 2023

Related U.S. Application Data

(63) Continuation of application No. 16/897,896, filed on Jun. 10, 2020, now Pat. No. 11,742,080.

(51) Int. Cl.
*G16H 40/63* (2018.01)
*A61M 1/14* (2006.01)
(Continued)

(52) U.S. Cl.
CPC ............ *G16H 40/63* (2018.01); *A61M 1/159* (2022.05); *A61M 1/282* (2014.02); (Continued)

(58) Field of Classification Search
CPC ...... G09B 23/28; G16H 40/63; A61B 5/0031; A61B 5/14542; A61B 5/026; (Continued)

(56) References Cited

U.S. PATENT DOCUMENTS 9,775,520 B2 * 10/2017 Tran ......................... A43B 3/48
9,993,169 B2 * 6/2018 Kotanko ............. A61M 1/3656
(Continued)

FOREIGN PATENT DOCUMENTS

AU 2018201518 A1 * 3/2018 .......... A61M 1/3656
CA 3057979 A1 * 10/2018 .......... A61B 5/1455
(Continued)

OTHER PUBLICATIONS

International Preliminary Report on Patentability in International Appln. No. PCT/US2021/036618, mailed Dec. 22, 2022, 8 pages.
(Continued)

*Primary Examiner* — Dilek B Cobanoglu
(74) *Attorney, Agent, or Firm* — Fish & Richardson P.C.

(57) ABSTRACT

A secure artificial intelligence (AI) enabled wearable medical sensor platform is used for adaptive operation according to features and techniques described herein. Operational parameters are modified based on data inputs thereto that provide feedback to the AI systems of the wearable sensor platform. The described technology can facilitate adaptive optimizations provided by AI machine learning algorithms in a manner that can beneficially assist in the monitoring and treatment of a patient. For example, the system described herein may be used for the continuous monitoring of the physiological parameters and health of a patient's vascular access point (for example, the fistula) and may provide, among other things, early warnings of possible infection at the vascular access location.

20 Claims, 15 Drawing Sheets

(51) Int. Cl.

| | |
|---|---|
| ***A61M 1/28*** | (2006.01) |
| ***A61M 1/34*** | (2006.01) |
| ***A61M 1/36*** | (2006.01) |
| ***G08B 21/18*** | (2006.01) |
| ***G16H 10/60*** | (2018.01) |
| ***G16H 20/40*** | (2018.01) |
| ***G16H 50/20*** | (2018.01) |
| ***G16H 50/70*** | (2018.01) |
| ***G16H 70/60*** | (2018.01) |
| ***H04L 9/08*** | (2006.01) |
| ***H04W 12/033*** | (2021.01) |
| *G08B 5/22* | (2006.01) |

(52) U.S. Cl.
CPC ........ *A61M 1/3403* (2014.02); *A61M 1/3655* (2013.01); *G08B 21/182* (2013.01); *G16H 10/60* (2018.01); *G16H 20/40* (2018.01); *G16H 50/20* (2018.01); *G16H 50/70* (2018.01); *G16H 70/60* (2018.01); *H04L 9/0819* (2013.01); *H04W 12/033* (2021.01); *A61M 1/152* (2022.05); *A61M 2205/18* (2013.01); *A61M 2205/50* (2013.01); *A61M 2230/20* (2013.01); *A61M 2230/30* (2013.01); *A61M 2230/50* (2013.01); *G08B 5/22* (2013.01)

(58) Field of Classification Search
CPC ... A61B 5/4848; A61B 5/14546; G06F 3/016; G06F 18/20; A43B 3/48; A61M 1/3656
USPC .......................................................... 705/2, 3
See application file for complete search history.

(56) References Cited

U.S. PATENT DOCUMENTS

| | | | | |
|---|---|---|---|---|
| 11,160,503 B2 * | 11/2021 | Peesapati | A61B 5/4848 | |
| 11,974,835 B2 * | 5/2024 | Stewart | A61B 5/026 | |
| 2001/0003793 A1 * | 6/2001 | Steuer | A61B 5/14546 | 600/479 |
| 2004/0120557 A1 * | 6/2004 | Sabol | G09B 23/28 | 382/128 |
| 2007/0175828 A1 * | 8/2007 | Goedje | A61M 1/30 | 600/481 |
| 2013/0211206 A1 * | 8/2013 | Sands | G16H 40/63 | 600/301 |
| 2014/0276027 A1 * | 9/2014 | Gaddis | A61B 5/4848 | 600/459 |
| 2017/0119258 A1 * | 5/2017 | Kotanko | G06T 7/20 | |
| 2018/0113498 A1 | 4/2018 | Cronin et al. | | |
| 2019/0095793 A1 | 3/2019 | Fink | | |
| 2019/0110696 A1 * | 4/2019 | Benkowski | A61B 5/0031 | |
| 2019/0220166 A1 * | 7/2019 | Nagaraju | G06F 3/016 | |
| 2019/0231199 A1 | 8/2019 | Al-Ali et al. | | |
| 2019/0324433 A1 * | 10/2019 | Cella | G06F 18/20 | |
| 2020/0197592 A1 | 6/2020 | Leinfellner et al. | | |
| 2020/0337638 A1 * | 10/2020 | Peesapati | A61B 5/14542 | |

FOREIGN PATENT DOCUMENTS

| | | | | | |
|---|---|---|---|---|---|
| CN | 104936517 A | * | 9/2015 | A61B 8/0841 |
| CN | 106184520 | | 12/2016 | |
| EP | 2919829 B1 | * | 2/2017 | A61M 1/1603 |
| TW | M564457 U | * | 8/2018 | |
| WO | WO 2018/053461 | | 3/2018 | |
| WO | WO-2018053461 A1 | * | 3/2018 | A61M 1/3641 |
| WO | WO 2020/165108 | | 8/2020 | |
| WO | WO-2020165108 A1 | * | 8/2020 | |
| WO | WO-2021108517 A1 | * | 6/2021 | A61M 1/3656 |

OTHER PUBLICATIONS

International Search Report and Written Opinion in International Appln. No. PCT/US2021/036618, mailed Sep. 16, 2021, 13 pages.

* cited by examiner

SECURE ARTIFICIAL INTELLIGENCE ENABLED MEDICAL SENSOR PLATFORMS

CROSS-REFERENCE TO RELATED APPLICATIONS

This application is a continuation application of and claims the benefit of priority to U.S. application Ser. No. 16/897,896, filed on Jun. 10, 2020, the contents of which are hereby incorporated by reference.

TECHNICAL FIELD

This disclosure generally relates to sensor platforms for monitoring the health of a user including secure artificial intelligence (AI) enabled wearable sensor platforms.

BACKGROUND

Patients with kidney failure or partial kidney failure typically undergo dialysis treatment using medical devices such as dialysis machines. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. Before the blood is returned to the body, air bubbles are removed from the blood to inhibit embolisms. The process of removing air is typically accomplished through use of a venous drip chamber, which is located downstream of the blood outlet of a dialyzer and upstream of the venous blood return of the patient.

During peritoneal dialysis, the patient's peritoneal cavity is periodically infused with dialysate, or dialysis solution. The membranous lining of the patient's peritoneum acts as a natural semi-permeable membrane that allows diffusion and osmosis exchanges to take place between the solution and the blood stream. Automated peritoneal dialysis machines, also called PD cyclers, are designed to control the entire peritoneal dialysis process so that it can be performed at home, usually overnight, without clinical staff in attendance. Both HD and PD machines may include displays with touch screens or other user interfaces that display information of a dialysis treatment and/or enable an operator or patient to interact with the machine.

When healthy, kidneys maintain the body's internal equilibrium of water and minerals (e.g., sodium, potassium, chloride, calcium, phosphorous, magnesium, and sulfate). In hemodialysis, blood is taken from a patient through an intake needle (or catheter) which draws blood from an artery located in a specific accepted access location (arm, thigh, subclavian, etc.). The drawn blood is pumped through extracorporeal tubing via a peristaltic pump, and then through a special filter called a dialyzer. The dialyzer is intended to remove unwanted toxins such as blood urea, nitrogen, potassium, and excess water from the blood. The dialyzed blood then flows out of the dialyzer via tubing and a needle (or catheter) back into the patient.

Vascular access is used for hemodialysis. These accesses are expected to sustain blood flow rates above 300 mL/min. One type of access is the arteriovenous fistula (AVF). AVF is considered to be the most effective of the vascular accesses for dialysis patients. One reason AVFs are effective is that they use native blood vessels, which, compared to synthetic grafts, are less likely to develop stenosis and fail. AVFs for hemodialysis typically include a surgically created connection between an artery and a vein in the arm. Artery walls are thicker than vein walls, and since the AVF connects the artery and the vein, the walls of the veins become thicker due to higher arterial pressure. The strengthened vein can then tolerate needles during hemodialysis.

Many different types of systems benefit from adaptive operation that is provided when used with artificial intelligence. In such systems, operational parameters are modified based on data inputs thereto that provide feedback to the artificial intelligence systems.

SUMMARY

In at least one aspect of the present disclosure a wearable sensor platform is provided. The wearable sensor platform includes: a plurality of sensors configured to capture raw sensor data; a transceiver; one or more storage devices storing computer-executable instructions; and one or more computer processors configured to execute the computer-executable instructions to cause the one or more computer processors to perform operations. The operations include: adjusting, using a machine learning model, one or more algorithms for processing the captured raw sensor data based on user data of a user of the wearable sensor platform; receiving the captured raw sensor data from the one or more sensors; determining, using the adjusted one or more algorithms and based on the captured raw sensor data, differential readings between pairs of sensors of the plurality of sensors; determining, using the adjusted one or more algorithms, whether the differential readings exceed a threshold; and generating an alert in response to determining that the differential readings exceed the threshold.

The operations can further include: receiving constraint data indicating one or more constraints corresponding to the wearable sensor platform; and applying the constraint data to the machine learning model during the adjusting. The operations can further include receiving, from an external source, one or more encryption keys; encrypting, use the one or more encryption keys, the captured raw sensor data; and transmitting the captured raw sensor data to the external source using the transceiver. The external source can include one or more processors of a dialysis system. The one or more encryption keys can include one or more multi-mode encoded keys. The threshold can be based on baseline reference data of the user learned by the machine learning model. The operations can further include: determining, using the adjusted one or more algorithms and based on the captured sensor data, whether one or more physiological measurements of the user deviate from a nominal value by a second threshold; and determining, in response to determining that one or more physiological measurements of the user deviated from the nominal value by the second threshold, trend information for the one or more physiological measurements, the trend information indicating a change in the one or more physiological measurements over time.

These and other aspects, features, and implementations can be expressed as methods, apparatus, systems, components, program products, methods of doing business, means or steps for performing a function, and in other ways, and will become apparent from the following descriptions, including the claims.

Implementations can include one or more of the following advantages. Continuous monitoring of the physiological parameters and health of a patient can be accomplished to provide, among other things, early warnings of possible problems. The described technology can facilitate adaptive optimizations provided by machine learning algorithms in a manner that can assist in providing a physiological profile tuned to a user's natural physical state while a sensor system retains validated baseline parameters and a baseline threshold derived from, for example, national standards. The described technology further provides for enhanced security related to the capture and use of a patient's data.

For example, the system described herein may be used for the continuous monitoring of the physiological parameters and health of a patient's vascular access point (for example, the fistula) and may provide, among other things, early warnings of possible infection at the vascular access location. Critical physical (corporal) characteristics near a patient's access point can be continuously monitored. The described technology can be used to increase cost saving in maintaining a vascular access point of the user. Further, the described technology can be used to increase the blood transfer efficiency through the vascular access point, and increase the lifespan and reduction in maintenance cost related to the vascular access point.

These and other aspects, features, and implementations will become apparent from the following descriptions, including the claims.

DETAILED DESCRIPTION

Figure 1:
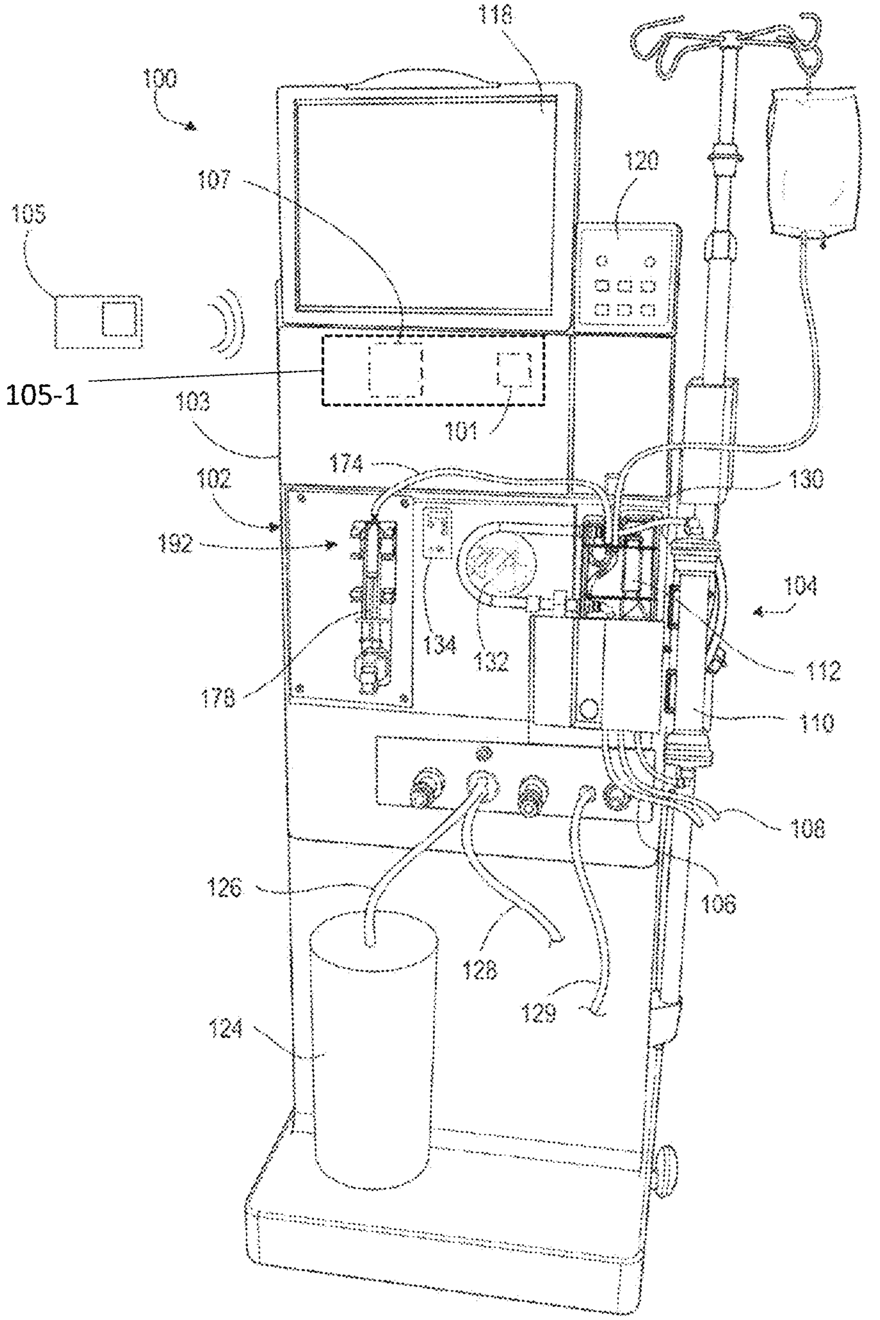
FIG. 1 shows a perspective view of a hemodialysis system, according to one or more implementations of the present disclosure.

A secure AI enabled wearable medical sensor platform may be used for adaptive operation according to features and techniques described herein. Operational parameters are modified based on data inputs thereto that provide feedback to the AI systems of the wearable sensor platform. The described technology can facilitate adaptive optimizations provided by AI machine learning algorithms in a manner that can beneficially assist in the monitoring and treatment of a patient. For example, the system described herein may be used for the continuous monitoring of the physiological parameters and health of a patient's vascular access point (for example, the fistula) and may provide, among other things, early warnings of possible infection at the vascular access location.

Although AVFs are effective accesses for patients undergoing hemodialysis, there are constraints that lead AVFs to fail. AVFs can become infected because they are exposed sites that facilitate removing blood from patients and reintroducing blood to the patients. Patients undergo hemodialysis about three times a week so there are multiple opportunities during the week for the AVF to become infected. Furthermore, AVFs can fail due to stenosis, improper maintenance during maturation period, hematoma, and a patient's overall lack of awareness. Typically, current AVF monitoring technologies are not wearable and do not perform continuous monitoring functions. Also, current AVF monitoring technologies can be invasive and are usually performed once every four weeks (and/or while a patient is receiving dialysis treatment). In these technologies, blood is recirculated, and an ultrasound or ultrasonic sensor is used to monitor the blood recirculation to determine whether the AVF is performing well. These technologies may also need blood chemistry lab results to measure various chemical and biological parameters.

Furthermore, the effectiveness of dialysis can depend on the patient's chemical, biological, and physical characteristics. A relatively healthy kidney may include natural biological sensory that can facilitate the maintenance of a patient's corporeal wellbeing, such as blood pressure control and production of hemoglobin. However, in a patient with chronic kidney disease (CKD), many of these natural biological sensors can become ineffective, and the corresponding natural corporeal sensory feedback control mechanisms can become less effective. For example, the lack of effective natural sensors embedded in the kidney can introduce unpredictable and/or unmanageable changes in the state of natural health of the patient (e.g., deficiency in blood pressure control, deficiency in the rate of hemoglobin production, and so forth). Furthermore, in systems that implement AI-machine learning, operational parameters can be modified based on sensor data inputs that provide feedback to the machine learning systems. For example, a speech recognition system may adapt and improve based on data input that indicates successes and failures. The adaptive optimizations may be provided by artificial intelligence processing that revises operation states of the speech recognition system. However, the adaptive optimizations may cause the systems to operate outside of design parameters that impact safety considerations. Also, raw patient data may include sensitive information, and the collection and distribution of such data may raise privacy concerns.

Implementations of the present disclosure can provide means to alleviate some of the aforementioned disadvantages. Some implementations of the present disclosure provide a secure AI enabled wearable sensor platform designed to utilize different sensors to detect onset of infection growth, clots from stenosis, and changes in the local area occurring due to improper maintenance. Some implementations of the present disclosure provide subjective assessments for whether an AVF is fine or whether an AVF is at risk. Some implementations of the present disclosure alert a clinic or an emergency contact to intervene when the AVF is at risk. As such, the intervention can come at a timely fashion to prevent further damage to the AVF. The patient's AVF can, therefore, be monitored more frequently, even continuously, as opposed to every four weeks in conventional methods.

Implementations of the present disclosure can provide systems and devices (for example, a secure AI enabled wearable sensor platform) that use machine learning to continuously track and monitor one or more sensors distributed near a patient's fistula. In some implementations, the described systems and devices use an AI assisted feedback control system (sometimes referred to as an analog front end in this specification) to optimize sensor response characteristics for a specific target objective. In some implementations, the described systems and devices use an AI assisted sensor sampling rate to optimize power usage for specific operational goals, track and monitor sensor performance, and track and monitor calibration data. In some implementations, the described systems and methods use AI assisted signal processing to provide suggestions for a medical professional (for example, a physician overseeing dialysis treatment) that may be used by the medical professional to optimize treatment prescription data. In some implementations, the described systems and devices can perform AI assisted system root-cause analysis and/or determine sensor degradation status, and can include supervisory features to limit AI control features to be within original factory validated/acceptance states.

The types of sensors used can be mapped to the natural biological sensors that may have become degraded or ineffective due to physiological/medical abnormalities. For example, the one or more sensors can include, among others, one or more of the following: a temperature sensor, pulse oximetry (SpO2) sensor, blood pressure sensor, blood flow rate sensor, phosphorous sensors, sodium sensors, and potassium sensors. Implementations of the described systems and devices can periodically determine the health of the access point (fistula) by determining one or more health parameters associated with the fistula, such as optimal transfer rate, likelihood of infection, and so forth. Implementations of the described systems and devices can determine one or more health parameters associated with a natural balanced corporeal operational state of the fistula that may have a vital impact on dialysis transfer efficiency (for example, natural body temperature, blood pressure, SpO2, erythropoietin level, blood flow rate, and so forth). Implementations of the present disclosure can determine the corporal operational state while the patient is undergoing dialysis, or when the patient is not undergoing dialysis.

Implementations of the present disclosure can use secure hash algorithms (SHAs), such as SHA-256 algorithms, to provide secure key based modification (and/or ability to enable/disable) of operational/functional features of AI supervisory functions, calibration algorithms, data/signal processing algorithms, and boundary conditions for the machine learning system to maintain deterministic operational stability of the entire platform. SHA-256 based multimode encoded key algorithms can be used to authenticate each device to a unique patient, patient's treatment data with respect to each dialysis treatment (and dialysis machine), while protecting patient specific data (utilizing traceable security keys and signature metadata) and maintaining safe operating limits. Implementations of the present disclosure can also manage and deploy fault tolerant SHA-256 based "multimode encoded security keys" (e.g., traceable keys) that facilitate remote software updates, remote configuration management, and remote secure data transfer and management.

Implementations of the present disclosure can provide one or more of the following functionalities. Infection growths near patient access points can be monitored and prevented. Clots from stenosis can be monitored and detected. Preemptive interventions to fix an AVF can be facilitated. Continuous feedback can be provided to patients for self-management, safety triggered "call back message" (for example, when potassium levels exceed safe limits, blood pressure changes exceed the safe limits, etc.), which can provide feedback for the clinic/physician when the patient is away from the dialysis machine. Continuous kidney sensory related data can be provided to a physician during or after dialysis treatments. Furthermore, in some implementations, when a secure AI enabled wearable sensor platform is within the proximity of a security engine platform (which can be installed in dialysis machine), it can receive, after authentication and handshake protocols, raw sensor data (while away from dialysis and in-dialysis), processed sensor data for suggestions to the physician (for example, indicating key characteristics, trends, etc.), sensor system signature metadata (for example, per request from the Security Engine Platform), or a combination of them, among others.

In the following description, for the purposes of explanation, numerous specific details are set forth in order to provide a thorough understanding of the present disclosure. It will be apparent, however, that the present disclosure may be practiced without these specific details. In other instances, well-known structures and devices are shown in block diagram form in order to avoid unnecessarily obscuring the present disclosure.

In the drawings, specific arrangements or orderings of schematic elements, such as those representing devices, modules, instruction blocks, and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships, or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

Several features are described hereafter that can each be used independently of one another or with any combination of other features. However, any individual feature may not provide any of the advantages discussed above or may provide one of the advantages discussed above. Although headings are provided, data related to a particular heading, but not found in the section having that heading, may also be found elsewhere in this description.

FIG. 1 shows a perspective view of a hemodialysis system 100 that includes a hemodialysis machine 102 connected to a disposable blood component set 104 that partially forms a blood circuit. During hemodialysis treatment, an operator connects arterial and venous patient lines 106, 108 of the blood component set 104 to a patient. The blood component set 104 includes an air release device 112, which contains a self-sealing vent assembly that allows air but does not allow liquid to pass. As a result, if blood passing through the blood circuit during treatment contains air, the air release device 112 will vent the air to atmosphere.

The blood component set 104 is secured to a module 130 attached to the front of the hemodialysis machine 102. The module 130 includes the blood pump 132 capable of circulating blood through the blood circuit. The module 130 also includes various other instruments capable of monitoring the blood flowing through the blood circuit. The module 130 includes a door that when closed, as shown in FIG. 1, cooperates with the front face of the module 130 to form a compartment sized and shaped to receive the blood component set 104. In the closed position, the door presses certain blood components of the blood component set 104 against corresponding instruments exposed on the front face of the module 130.

The operator uses a blood pump module 134 to operate the blood pump 132. The blood pump module 134 may include a display window, a start/stop key, an up key, a down key, a level adjust key, and an arterial pressure port. The display window displays the blood flow rate setting during blood pump operation. The start/stop key starts and stops the blood pump 132. The up and down keys increase and decrease the speed of the blood pump 132. The level adjust key raises a level of fluid in an arterial drip chamber. The controls may exist as physical buttons/switches/actuators/ etc. or wholly within a graphical user interface on a touch screen accessible display 118 or some combination thereof.

The hemodialysis machine 102 further includes a dialysate circuit formed by the dialyzer 110, various other dialysate components, and dialysate lines connected to the hemodialysis machine 102. Many of these dialysate components and dialysate lines are inside the housing 103 of the hemodialysis machine 102 and are thus not visible in FIG. 1. During treatment, while the blood pump 132 circulates blood through the blood circuit, dialysate pumps (not shown) circulate dialysate through the dialysate circuit.

A dialysate container 124 is connected to the hemodialysis machine 102 via a dialysate supply line 126. A drain line 128 and an ultrafiltration line 129 also extend from the hemodialysis machine 102. The dialysate supply line 126, the drain line 128, and the ultrafiltration line 129 are fluidly connected to the various dialysate components and dialysate lines inside the housing 103 of the hemodialysis machine 102 that form part of the dialysate circuit. During hemodialysis, the dialysate supply line 126 carries fresh dialysate from the dialysate container 124 to the portion of the dialysate circuit located inside the hemodialysis machine 102. As noted above, the fresh dialysate is circulated through various dialysate lines and dialysate components, including the dialyzer 110, that form the dialysate circuit. As will be described later, as the dialysate passes through the dialyzer 110, it collects toxins from the patient's blood. The resulting spent dialysate is carried from the dialysate circuit to a drain via the drain line 128. When ultrafiltration is performed during treatment, a combination of spent dialysate (described below) and excess fluid drawn from the patient is carried to the drain via the ultrafiltration line 129.

The dialyzer 110 serves as a filter for the patient's blood. The dialysate passes through the dialyzer 110 along with the blood, as described above. A semi-permeable structure (e.g., a semi-permeable membrane and/or semi-permeable microtubes) within the dialyzer 110 separates blood and dialysate passing through the dialyzer 110. This arrangement allows the dialysate to collect toxins from the patient's blood. The filtered blood exiting the dialyzer 110 is returned to the patient. The dialysate exiting the dialyzer 110 includes toxins removed from the blood and is commonly referred to as "spent dialysate." The spent dialysate is routed from the dialyzer 110 to a drain.

A drug pump 192 also extends from the front of the hemodialysis machine 102. The drug pump 192 is a syringe pump that includes a clamping mechanism configured to retain a syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via a drug delivery line 174 during use, or to draw liquid from the blood circuit into the syringe 178 via the drug delivery line 174 during use.

The hemodialysis machine 102 includes a security engine platform 105-1 that includes a control unit 101 (e.g., a processor) configured to receive signals from and transmit signals to the display 118, the control panel 120, and a communication module 107 (e.g., a near field communication (NFC) transceiver). The control unit 101 can also communicate with a network, server (e.g., an Internet server), or a master design and test platform (for example, as described later in this specification). In some implementations, the control unit 101 controls operating parameters of the hemodialysis machine 102 based at least in part on signals received by the display 118, the control panel 120, and the communication module 107.

The display 118 presents a user interface that may include vital signs of a patient, operational parameters of the dialysis treatment, and controls associated with the hemodialysis process. For example, the operational parameters may include ultrafiltration parameters, blood pump rate and information associated with the dialysate, hematocrit alert levels, blood pressure alarm limits, medicine infusion parameters, etc. The display 118 may include a touch screen through which the operator may interact and control the hemodialysis machine 102. For example, the operator may input various treatment parameters associated with the hemodialysis process.

The communication module 107 is configured to detect and communicate with an authenticated short-range wireless device—for example, an ID card 105, smart card, mobile device (for example, a smartphone belonging to a patient of medical care professional), and/or one of the wearable secure AI enabled sensor platforms described in this specification—when the device is within its wireless communication range. The communication module 107 is capable of communicating (for example, through multimode encoded security keys) information associated with the patient to the control unit 101. The communication module 107 can send a signal to the control unit 101 indicating that the patient is no longer present.

The control unit 101 is capable of receiving information (for example, through multimode encoded keys) associated with the identity of the patient from the communication module 107 and comparing the information with authentication profiles for multiple users (for example, patients) stored in a database. The database may be stored on a storage device associated with the dialysis system 100 or located at an external storage device (for example a server or a storage device associated with a different dialysis system.) Based on the comparison, the control unit 101 may retrieve the interface configuration profile of the operator or patient. The specific user interface that appears on the display may be based on the retrieved interface configuration profile. For example, the operating parameters and the dialysis controls that constitute the user interface may be determined from the retrieved interface configuration profile. Additionally, identity of the operator or patient, and the identity of a supervisor of the operator may also be displayed.

The control unit 101 is capable of communicating information associated with identity of the patient and a secure AI enabled wearable sensor platform (such as one or more of the wearable sensor platforms described later in this specification). The control unit 101, with a command and control instruction (for example, received from a master design and test platform described in this specification) is capable of adding or modifying an interface and/or operation configuration profile. The control unit 101 may be configured to detect an alert or alarm (used interchangeably herein) in the hemodialysis system 100, and based on the alarm, change the user interface that appears on the display 118 (for example, an alarm specific to a security and/or system anomaly). The alarm may be caused when the value of an operational parameter satisfies a criteria. For example, an alarm may occur when conductivity of the dialysate is above a certain value. This may require immediate attention from a nurse, and therefore the user interface that appears on the display 118 may be changed to a form expected by and/or familiar to the nurse.

Figure 2:
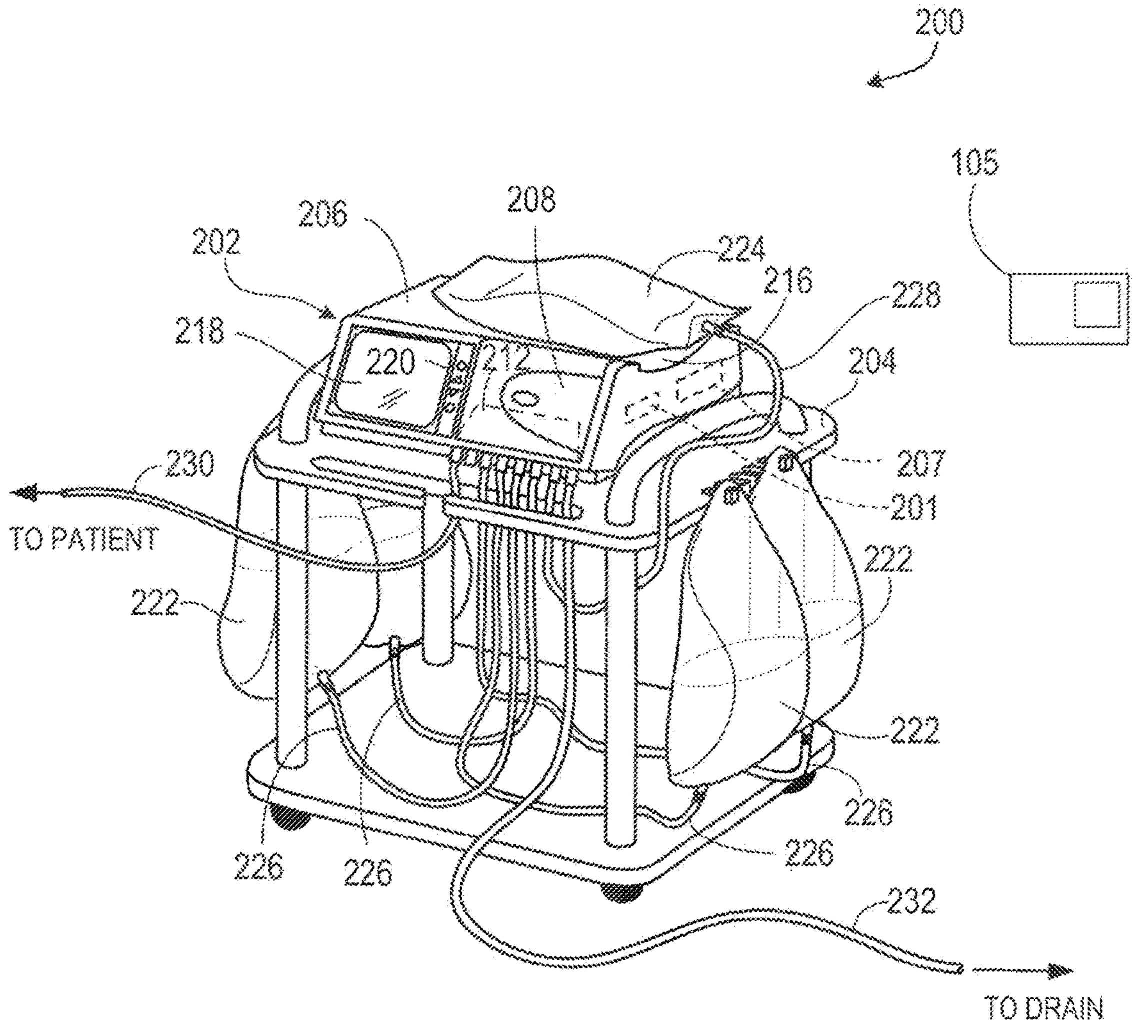
FIG. 2 shows a perspective view of a peritoneal dialysis system, according to one or more implementations of the present disclosure.

FIG. 2 shows a perspective view of a peritoneal dialysis (PD) system 200 that includes a PD cycler (also referred to as a PD machine) 202 seated on a cart 204. The PD cycler 202 includes a housing 206, a door 208, and a cassette interface (not shown) that contacts a disposable PD cassette 212 when the cassette 212 is disposed within a cassette compartment formed between the cassette interface and the closed door 208. A heater tray 216 is positioned on top of the housing 206. The heater tray 216 is sized and shaped to accommodate a bag of dialysate (e.g., a 5 liter bag of dialysate). The PD cycler 202 also includes a display 118 and additional control panel 220 that can be operated by a user (e.g., a patient) to allow, for example, set-up, initiation, and/or termination of a PD treatment.

Dialysate bags 222 are suspended from fingers on the sides of the cart 204, and a heater bag 224 is positioned in the heater tray 216. The dialysate bags 222 and the heater bag 224 are connected to the cassette 212 via dialysate bag lines 226 and a heater bag line 228, respectively. The dialysate bag lines 226 may be used to pass dialysate from dialysate bags 222 to the cassette 212 during use, and the heater bag line 228 may be used to pass dialysate back and forth between the cassette 212 and the heater bag 224 during use. In addition, a patient line 230 and a drain line 232 are connected to the cassette 212. The patient line 230 may be connected to a patient's abdomen via a catheter and may be used to pass dialysate back and forth between the cassette 212 and the patient's peritoneal cavity during use. The drain line 232 may be connected to a drain or drain receptacle and may be used to pass dialysate from the cassette 212 to the drain or drain receptacle during use. The various components that pass dialysate form a dialysate circuit.

The PD system 200, like the hemodialysis system 100, includes a control unit 201, a display 218 and a communication module 207 that communicate with one another, and with a short-range wireless device (for example, the ID card 105 or a smartphone). Similar to the hemodialysis system 100, the PD system 200, using components such as the control unit 201 and the communication module 207, may detect information associated with the identity of an operator or patient, and change the user interface that appears on the display 218 based on an interface configuration profile. The PD system 200 allows an operator or patient to add or modify the interface configuration profile that may be stored in a storage device associated with the PD system 200, or an external storage device (for example, a server). Furthermore, the control unit 201 of the PD system 200 may change the user interface that appears on the display 218 based on an alarm in the PD system 200.

Figure 3A:
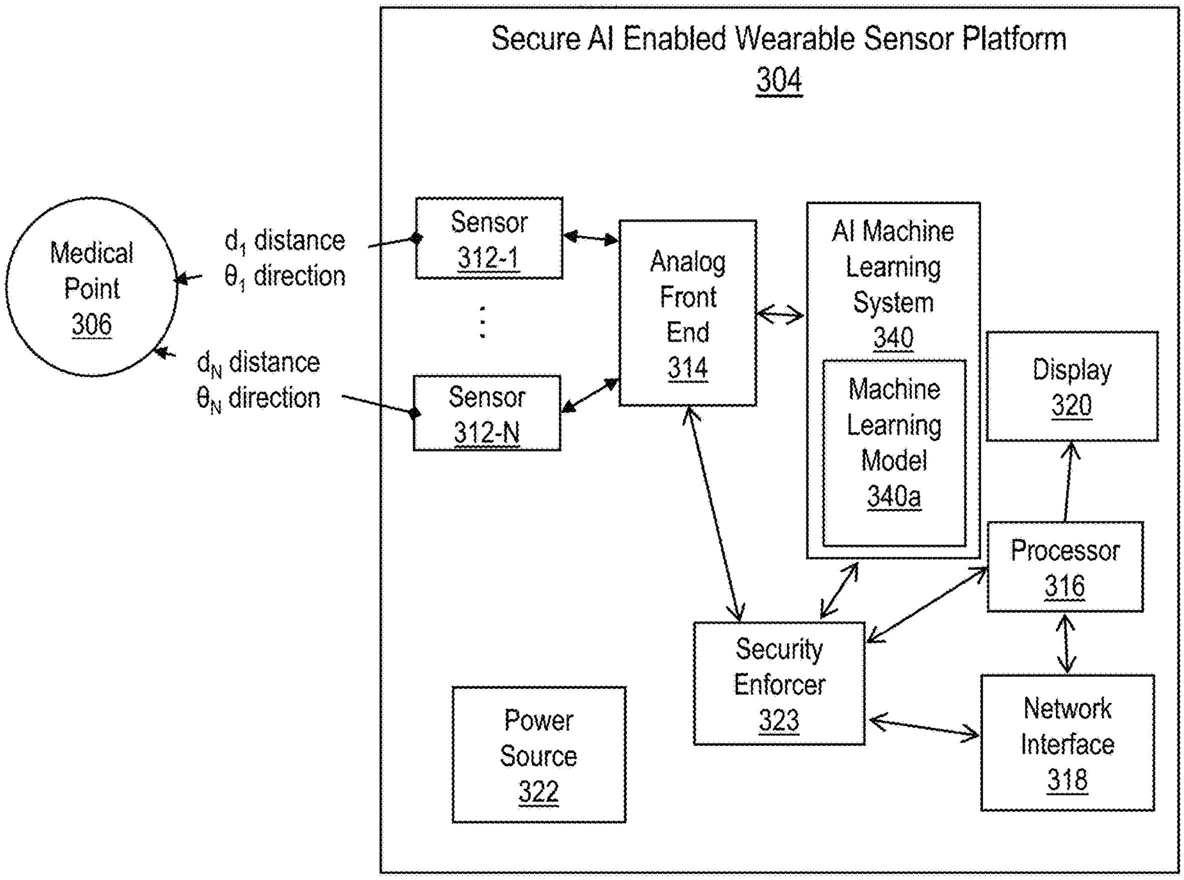
FIG. 3A shows a block diagram of a secure AI enabled wearable sensor platform, according to one or more implementations of the present disclosure.

FIG. 3A shows a block diagram of a secure AI enabled wearable sensor platform 304, according to one or more implementations of the present disclosure. The wearable sensor platform 304 includes two or more sensors 312-1 to 312-N (hereinafter collectively referred to as the sensors 312). The sensors may take measurements in connection with a medical area, site or point of interest 306, for example, an access point for an AVF. For example, using the center of the medical point (e.g. access point) 306 for orientation, each of the sensors 312 is located a distance $d_x$ from the access point 306 at a direction $\theta_x$. The sensors 312 generate sensor data by measuring conditions at specific locations relative to the location of the medical point 306. It is noted that the system described herein is discussed principally in connection with medical sensor platform worn on the arm, e.g. in connection with monitoring a vascular access site; however, the wearable sensor platform of the system described herein may be appropriately utilized in connection with other medical areas and points of interest for a patient, and may be configured to be wearable in locations and manners other than on the arm.

The sensors 312 can include two or more of pressure sensors, temperature sensors, oxygen saturation SpO2 sensors, color sensors (RGB color or XYZ spectral sensors), infrared (IR) sensors, ultrasonic time-of-flight sensors, force sensors like accelerometers, among others. For example, the sensors 312 can include a pulse oximetry (SpO2) sensor that uses a red light source, an infrared light source, photo detectors, and a probe to measure oxygen saturation of a patient's blood. The sensors 312 can include a combination of an RGB Color sensors, XYZ spectral sensors, and infrared sensors that can facilitate determining one or more of: Blood CO2 saturation levels, potassium (K) concentration and quantity, Phosphate (PO3) concentration and quantity, possibility of Anemia, possibility of Fistula Infection (e.g., Fistula health, transfer efficiency, and so forth), and other health parameters (e.g., hormone levels).

The sensors 312 can include MEMS ultrasonic time-of-flight sensors to facilitate determining one or more of: blood flow rate, blood vessel health (e.g., determine degradation amounts for veins, arteries, capillaries, and so forth), and blood vessel transfer efficiency. The sensors 312 can include temperature sensors to facilitate determining one or more of the following: correlations between infection and a healthy access point and patient body responses during and after dialysis. The sensors 312 can include MEMS pressure sensors to facilitate determining one or more of: heart beat rate, blood pressure, correlations between blood flow rate and blood pressure (e.g., in conjunction with MEMS ultrasonic time-of-flight sensors), and heart condition (e.g., in conjunction with MEMS ultrasonic time-of-flight sensors).

In some implementations, two or more of the sensors 312 are tunable/adaptable to measure a desired characteristic, in which the two or more tunable/adaptable sensors 312 are tuned to specific wavelengths appropriate for measuring the desired characteristic of a particular patient. For example, at least some of the sensors 312 and light sources can be tuned to wavelengths appropriate for measuring the potassium levels of a particular patient's blood based on information learned about the particular patient, and then be tuned to wavelengths appropriate for measuring the phosphorous levels of the particular patient's blood based on information learned about the particular patient. The tuning/adapting of sensors to a particular patient is described later in this specification.

The wearable sensor platform 304 includes an analog front end (AFE) 314 for conditioning and processing the sensor data generated. Signal conditioning by the analog front end 314 can include preparing signal levels of sensor data of each of sensors 312 so that analogous data can be compared. Signal conditioning can include applying a Nyquist filter to the sensor data. Signal processing of the sensor data by the analog front end 314 can include using tunable hardware filters capable of extracting stable data of interest with minimal noise. Signal processing can include signal-noise-ratio optimization. For example, RGB IR optical sensors can be packaged with an RGB IR light source. During design of the sensors (for example, during a algorithm and hardware design phase at a master design and test platform as described later in this specification), a testing process can be used that simulates a patient's skin surface. For each target of interest (for example, sodium, potassium, SPO2, etc.), there can be a corresponding spectral frequency response. For a spectral response, signal to noise ratio (SNR) may depend on gain, bandwidth, nature of scattering (reflecting) surface, movements (skin) of the reflecting surface, intensity of light source, ambient light, distance from the reflecting medium, electronic noise (from circuitry), ground noise from power source, surrounding electromagnetic noise induction, and so forth. Based on these factors, outputs of the sensors can be baselined.

Signal processing can include applying one or more tracking algorithms to the conditioned sensor data. The tracking algorithms can be adapted to a particular characteristic of interest. For example, a spectrometer sensor can be tuned to detect potassium based on baseline data and dynamic data collected from the patient through the wearable sensor platform 304. Tuning and tracking algorithms can be defined specific to a sensor and a measured objective (which is independent of patient specific data). Baseline reference data can be created using a master design and test platform by inducing several (or all) possible real-life scenarios/variables. For example, a spectral sensor utilizing absorption/scattering property can be burdened with noise artifacts from skin color, skin movements, and so forth. AI-machine learning systems at the master design and test platform can have tunable algorithms and can use ideal spectral response data as baseline input, and then determine all possible conditions that can affect SNR. AI-machine learning algorithms can be used to create a recognizable higher confidence level to track and measure a desired measurement and/or characteristics of interest (signature metadata). The baseline algorithm and data can create a reference profile for the measurement of interest. When the wearable senor platform 304 is on a patient, the sensor data can be received by an artificial intelligence (AI) machine learning system 340 of the wearable sensor platform 304, and the AI machine learning system 340 can create a signature metadata. The AI machine learning system 340 can be used to compare the sensor data with the baseline data and provide appropriate control parameters to control the analog front end 314 to get the sensor data that can be close to the baseline data (signature/profile) created using the Master Design and Test Platform. This continuous real-time learning and continuous tuning to get optimized data (with optimized SNR) can provide predictive/deterministic measurements, increasing processing time while reducing power consumption (for the machine learning process).

Signal processing can also include one or more of applying sensor response/pattern reorganization algorithms to the conditioned sensor data and applying predictive algorithms to the conditioned sensor data. The analog front end 314 can include tunable filters that facilitate spectral response processing that can be adapted to a particular patient. The analog front end 314 can track the sensors and calibrate the sensors based on data obtained during tracking. The analog front end 314 can algorithmically control the sensors 312 to tune one or more of the sensors to a particular patient such that desired characteristics of the particular patient can be measured, as described previously (e.g., tune an RGB sensor to a particular range of wavelengths so that the sensor data can be used to measure a potassium concentration of the patient). In some implementations, the analog front end 314 applies sensor response/pattern reorganization and predictive algorithms to the sensor data. As will be explained later in this specification, the algorithms can be designed such that they do not infringe upon specified rules and boundary conditions.

The wearable sensor platform 304 includes a processor 316 which performs further preparation of the sensor data for transmission. The processor 316 can be an ultra-low power processor, a field programmable gate array (FPGA), a complex programmable logic device (CPLD), and so on.

The secure AI enabled wearable sensor platform 304 (sometimes referred to as a wearable sensor platform 304 in this specification) includes a wireless communications interface 318 (sometimes referred to as a communications interface 318 or interface 318 in this specification). The communications interface 318 allows communication with one or more external devices, such as a security engine platform residing on a dialysis system (as described previously with respect to FIGS. 1-2. The wearable sensor platform 304, after a successful authentication with a security engine platform, can send status and monitoring data prepared by the security engine platform. The wearable sensor platform 304 can also receive configuration updates, software updates, and calibration updates from the security engine platform. The interface 318 can includes radio frequency transceivers. Examples of interfaces 318 include radio transceivers compatible with several Wi-Fi standards, cellular modems, and so forth.

The wearable sensor platform 304 includes a display 320. The display 320 can include one or more light emitting diode (LED) lights for providing visual indications. The LED lights can indicate that the wearable sensor platform 304 is functioning/not functioning properly and/or the access point 306 is/isn't at risk. In some embodiments, since functioning properly is expected most of the time, the LED lights only turn on to indicate that something is wrong; this way, the LED lights do not consume energy during normal operation. The display 320 can also include one or more auditory indicators like a speaker that beeps when the wearable sensor platform 304 is either not functioning properly or when the access point 306 is at risk. In some embodiments, the display 320 provides a visual and/or auditory indication when the wearable sensor platform 304 first comes online, when the wearable sensor platform 304 is proximate to the dialysis machine (e.g., when the wearable sensor platform 304 detects the presence of the security engine platform by handshake protocols), and when blood flow rate sensor data profiles match to flow rate data during a dialysis treatment.

The wearable sensor platform 304 includes a power source 322 for providing power to the different components described. In some embodiments, the power source 322 is a battery or a rechargeable battery.

The wearable sensor platform 304 includes a security enforcer 323. Generally, the security enforcer 323 is capable of facilitating the updating of the AI machine learning system 340 using a key-based authentication scheme, guard-banding operational/control limits governed by the AI machine learning system 340, providing data (e.g., raw sensor data and process data) to a physician (e.g., via a security engine platform residing in a dialysis system) to assist the physician in deriving quicker and effective decisions regarding a patient and treatments (e.g., prescriptions). The security enforces is also generally capable of autonomously facilitating warning/messaging decisions when any of the data measured by the sensors 312 triggers a critical safety state (e.g., blood pressure reading exceeds safe low and high limits).

The security enforcer 323 is programmable hardware, e.g., an FPGA or a CPLD that serves one or more functions. In some implementations, the security enforcer 323 performs platform management, power management, and security enforcement. For platform management, the security enforcer 323 manages system level critical tasks for the wearable sensor platform 304. Platform management can include ensuring sensor data integrity and operational stability control. For example, the security enforcer 323 receives data from the sensor 312-1. The data from the sensor 312-1 is appended with an authentication code where the security enforcer 323 checks this authentication code against a code from the sensor 312-1 to determine whether the data came from the specific sensor.

Platform management can also include monitoring safety critical status signals and critical signal integrity. Safety critical status signals are signals assigned to represent safe operating limits of the wearable sensor platform 304. An example includes power monitoring signals that define status of the power source 322. The power monitoring signals can indicate a remaining power level where the security enforcer 323 determines whether the remaining power level is adequate to provide trustable information from the sensors 312. For example, if remaining power level falls below a predefined level, then the security enforcer 323 enforces safety protocols. The safety protocols include operational safety protocols and/or human safety protocols. An operational safety protocol can involve storing present data, setting a warning indicator (e.g., blinking orange light from a tri-color LED of the status indicator 320), reducing sampling rate for the sensors 312, and reducing signal processing rate at the analog front end 314 and/or the processor 316. In some implementations, the security enforcer 323 performs human operational control, which can include sounding an alarm via speakers in the display 320 to check for a short circuit that can create high current and may cause burning.

In some embodiments, signal integrity of safety critical status signals cannot be trusted to enforce correct safety protocols. The security enforcer 323 determines whether the signal has too much noise susceptibility. Signals with too much noise susceptibility include, for example, unstable signals due to susceptibility to changes in ambient temperature and unstable signals due to electromagnetic compatibility (EMC) compliances. The security enforcer 323 also monitors abnormal loading of configuration and calibration data. In some implementations, authentication of the security enforcer 323 is required to modify the configuration and calibration data.

Platform management can also include emergency control enforcing for safety critical parameters and functionality. Platform management can also include sensor calibration status check with respect to stored baseline data. Platform management can also include control and retention of factory calibration data, sensor functional/operational configuration data, and/or the wearable sensor platform 304 functional/operational configuration data. Platform management can further include system alarm and safe operating limits management. Platform management can also include safeguarding boot code of the security enforcer 323 from corruption from one or more forms of unauthorized/undesired changes.

Power management of the security enforcer 323 involves power sequencing and reset processing, power monitoring, power management and optimizations for longer time-between-recharge and for performance optimizations, and power emergency controls. Power emergency controls include safety protocol management and safe management of sensor data when available operating power is below a safe operating threshold, as discussed above.

Security enforcement of the security enforcer 323 includes cybersecurity guard/compliance enforcement for secure and safe operation of hardware and software of the wearable sensor platform 304. Security enforcement includes security key management for master authentication and encryption and decryption engines for secure signal and/or data processing, transfer, and storage. In master authentication, a security key is transferred from a manufacturing site of the wearable sensor platform 304 (after factory acceptance tests) to authenticate and enable secure engine functionality. At the manufacturing site, device operational configuration files can be loaded, calibrated, and tested before approval for customer delivery. Security enforcement also includes threat monitoring and critical event logging, e.g., logging of safety and security events, logging of remote accesses to the wearable sensor platform, and so on. Security enforcement can also include a safety and security mode (including internal and external data management and communication/data transfer).

In some implementations, security enforcement includes receiving a multi-mode encoded key (e.g., traceable key) from an outside source (e.g., a standalone board residing in a dialysis machine). In some implementations, the multi-mode encoded key is designed by the manufacturing site (for example, a master design and test platform as described later in this specification). The multi-mode encoded key can correspond with a secure hash algorithm (SHA), such as an SHA256 algorithm. The security enforcer 323 can process the multimode encoded keys to generate an identification key particular to the patient using the wearable sensor platform 304, and use the identification key to encrypt the raw sensor data captured by the sensors 312, such that the encrypted raw sensor data is traceable to the particular patient. As will be described later, the encrypted raw sensor data can be transmitted to an outside source (e.g., a security engine platform as described in this specification) for further processing. The security enforcer 323 can also receive the multimode encoded keys from a security engine platform to authenticate the wearable sensor platform 304 to receive software updates from the security engine platform (e.g., updates to machine learning algorithms, rules and boundary conditions, and so forth, as explained later in more detail).

Security enforcement by the security enforcer 323 also includes supervising the AI machine learning system 340. For example, the security enforcer 323 can guard-band operational/control limits governed by the AI machine learning system 340, as described later in more detail. The guard-banding can, for example, ensure that algorithmic modifications to the sensors 312 and/or the analog front end 314 do not cause these components to operate outside of their pre-validated state (e.g., in accordance with validation performed by a manufacturer/Master Design and Test Platform, as described later in more detail).

The AI machine learning system 340 applies rules/goals based (e.g., baseline rules/goals that are designed and validated by a mater design and test platform) machine learning techniques to train the machine learning model 340*a* that, when applied to input data, generates indications of whether the input data items have an associated property or properties. As part of the training of the machine learning model 340*a*, the AI machine learning system 340 can form a training set of input data by identifying a positive training set of input data items that have been determined to have the property in question, and, in some implementations, forms a negative training set of input data items that lack the property in question.

The AI machine learning system 340 extracts values from the input data of the training set, the values being variables deemed potentially relevant to whether or not the input data items have the associated property or properties (e.g., defined by the rules/goals). An ordered list of the features for the input data is herein referred to as the feature vector for the input data. In some implementations, the AI machine learning system 340 applies dimensionality reduction (e.g., via linear discriminant analysis (LDA), principle component analysis (PCA), learned deep features from a neural network, or the like) to reduce the amount of data in the feature vectors for the input data to a smaller, more representative set of data.

In some implementations, the AI machine learning system 340 uses supervised machine learning (for example, at a master design and test platform to create baseline profile data for each sensors and corresponding measurements) to train the machine learning model 340*a* with the feature vectors of the positive training set and the negative training set serving as the inputs. Different machine learning techniques—such as linear support vector machine (linear SVM), boosting for other algorithms (e.g., AdaBoost), neural networks, logistic regression, naïve Bayes, memory-based learning, random forests, bagged trees, decision trees, boosted trees, or boosted stumps—are used in some implementations. The machine learning model 340*a*, when applied to the feature vector extracted from the input data item, outputs an indication of whether the input data item has the property in question, such as a Boolean yes/no estimate, a scalar value representing a probability, a vector of scalar values representing multiple properties, or a nonparametric distribution of scalar values representing different and not a priori fixed numbers of multiple properties, which may be represented either explicitly or implicitly in a Hilbert or similar infinite dimensional space.

In some implementations, a validation set is formed of additional input data, other than those in the training sets, which have already been determined to have or to lack the property in question. The AI machine learning system 340 applies the trained machine learning model 340*a* to the data of the validation set to quantify the accuracy of the machine learning model 340*a*. Common metrics applied in accuracy measurement include: Precision=TP/(TP+FP) and Recall=TP/(TP+FN), where precision is how many the machine learning model 340*a* correctly predicted (TP or true positives) out of the total it predicted (TP+FP or false positives), and recall is how many the machine learning model 340*a* correctly predicted (TP) out of the total number of input data items that did have the property in question (TP+FN or false negatives). The F score (F-score=2*PR/(P+R)) unifies precision and recall into a single measure. In some implementations, the machine learning system 340 iteratively re-trains the machine learning model 340*a* until the occurrence of a stopping condition, such as the accuracy measurement indication that the model 340*a* is sufficiently accurate, or a number of training rounds having taken place.

In some implementations, the machine learning model 340*a* includes a neural network. In some implementations, the neural network includes a convolutional neural network. The machine learning model 340*a* can include other types of neural networks, such as recurrent neural networks, radial basis function neural networks, physical neural networks (e.g., optical neural network), and so forth.

The machine learning model 340*a* is configured to modify, based on learned features particular to the patient using the wearable sensor platform 304, the algorithms used by the analog front end 314 to perform signal processing. For example, based on learned characteristics of the patient, the machine learning model 340*a* can tune the tunable filters of the analog front end 314 to a particular patient to facilitate adaptable spectral response processing. The machine learning model 340*a* can also update the user adaptable tracking algorithms and SNR optimization algorithms of the analog front end 314, based on learned characteristics of the patient. The machine learning model 340*a* can implement rules and boundary conditions set forth by the security enforcer 323 to ensure that any algorithmic updates do not cause the wearable sensor platform 304 to infringe validated states as set forth by a manufacturer/Master Design and Test Platform (described later). The machine learning model 340*a* can include a safe-operation look-up table that consists of operating parameters and limits related to basic safety and essential performances. The safe-operation look-up table can be used to create rules and constraints for the AI-machine learning system to protect against any system changes that will induce non-validated states or conditions for the platform 304. The machine learning model 340*a* can use function enable keys to facilitate changes or modifications, or enable/disable functionality with respect to the AI-machine learning system.

Figure 3B:
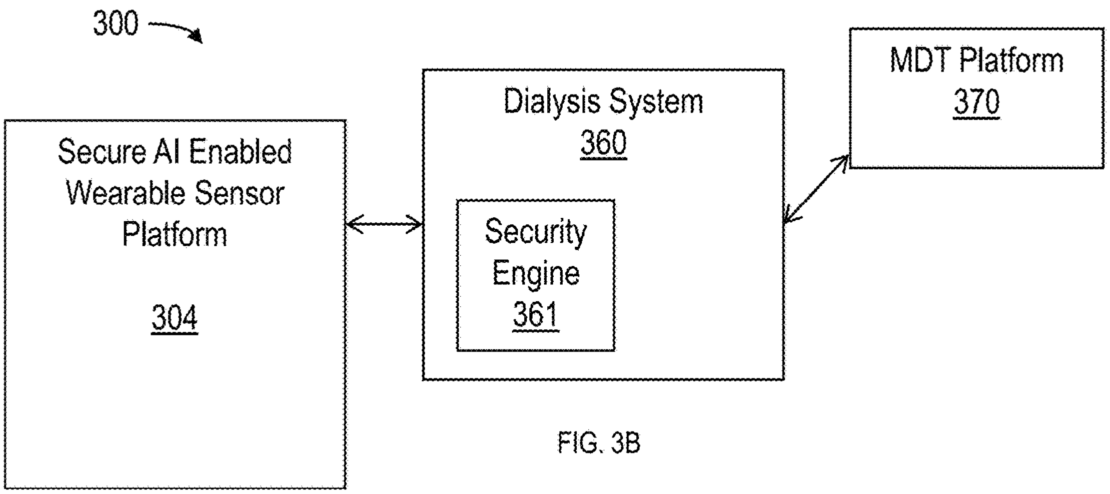
FIG. 3B shows a block diagram of an environment for monitoring a vascular access, according to one or more implementations of the present disclosure.

FIG. 3B shows a block diagram of an environment 300 for monitoring a vascular access, according to one or more implementations of the present disclosure. The environment includes and Master Design and Test (MDT) platform 370 (which can be integrated with a security engine platform 361), a dialysis system 360, and the wearable sensor platform 304 described previously with reference to FIG. 3A.

In general, the MDT platform 370 provides remote software updates and remote diagnostics for the wearable sensor platform 304 and the security engine platform 361 of the dialysis system 360. The MDT platform 370 is also generally capable of providing deep root-cause analysis for the security engine 361 of the dialysis system 360 and wearable sensor platform 304 (e.g., any root-cause analysis that is beyond the capabilities of the security engine platform 361 and wearable sensor platform 304). The MDT platform 370 is generally capable of providing the backbone for deep trend analysis and comparative (snapshot) studies among several security engines 361, along with continuous design improvements, rule/goal tables, and so forth.

The MDT platform 370 is configured to generate and validate the multi-mode encoded keys described previously with reference to FIG. 3A. The MDT platform 370 is configured to provide model based design and development environments for the design of hardware, software, and algorithms used with the wearable sensor platform 304 and the security engine platform 361 of the dialysis system 360, as well as the optimization, verification, and validation of such algorithms.

The dialysis system 360 can be similar to the dialysis systems 100, 200 described previously with reference to FIGS. 1-2. The dialysis system 360 includes the security engine platform 361, which can be a stand-alone board that resides in dialysis equipment of the dialysis system 360. The security engine platform 361 can authenticate the wearable sensor platform 304 and its functions. The security engine 361 can receive the multi-mode encoded keys from the MDT platform 370, and provide the keys to the wearable sensor platform 304 (e.g., when the wearable sensor platform 304 is within a close range due to the patient undergoing dialysis treatment). The security engine platform 361 can use the multi-mode encoded keys to authenticate and encrypt/decrypt data transferred between the security enforcer 323 of the wearable sensor platform 304 and the security engine 361. The security engine platform 361 is configured to perform software updates and lifecycle management of the wearable sensor platform 304. The security engine platform 361 is configured to receive one or more of: the captured raw sensor data from the wearable sensor platform 304 and the processed sensor data from the wearable sensor platform 304. As indicated previously, the captured raw sensor data and/or the processed sensor data can be encrypted by the wearable sensor platform 304 (e.g., using the security enforcer 323) with a multi-mode encoded keys. In some implementations, the security engine platform 361 can include corresponding multi-mode encoded keys which can be used to decrypt the received data. The security engine 361 can transmit the received data to the MDT platform 370 before or after encryption. In some implementations, the MDT platform 370 includes corresponding multi-mode encoded keys for decrypting the data. As indicated previously, the processed sensor data can include intelligent information. The security engine 361 can provide the raw captured data and the processed sensor data, along with encrypted prescription data representing prescriptions used by the dialysis system 360 to perform treatment and performance data indicating how the dialysis system 360 performed for a specific prescription, to a physician (e.g., to an electronic device of the physician or through a user interface of the dialysis machine).

Figure 4:
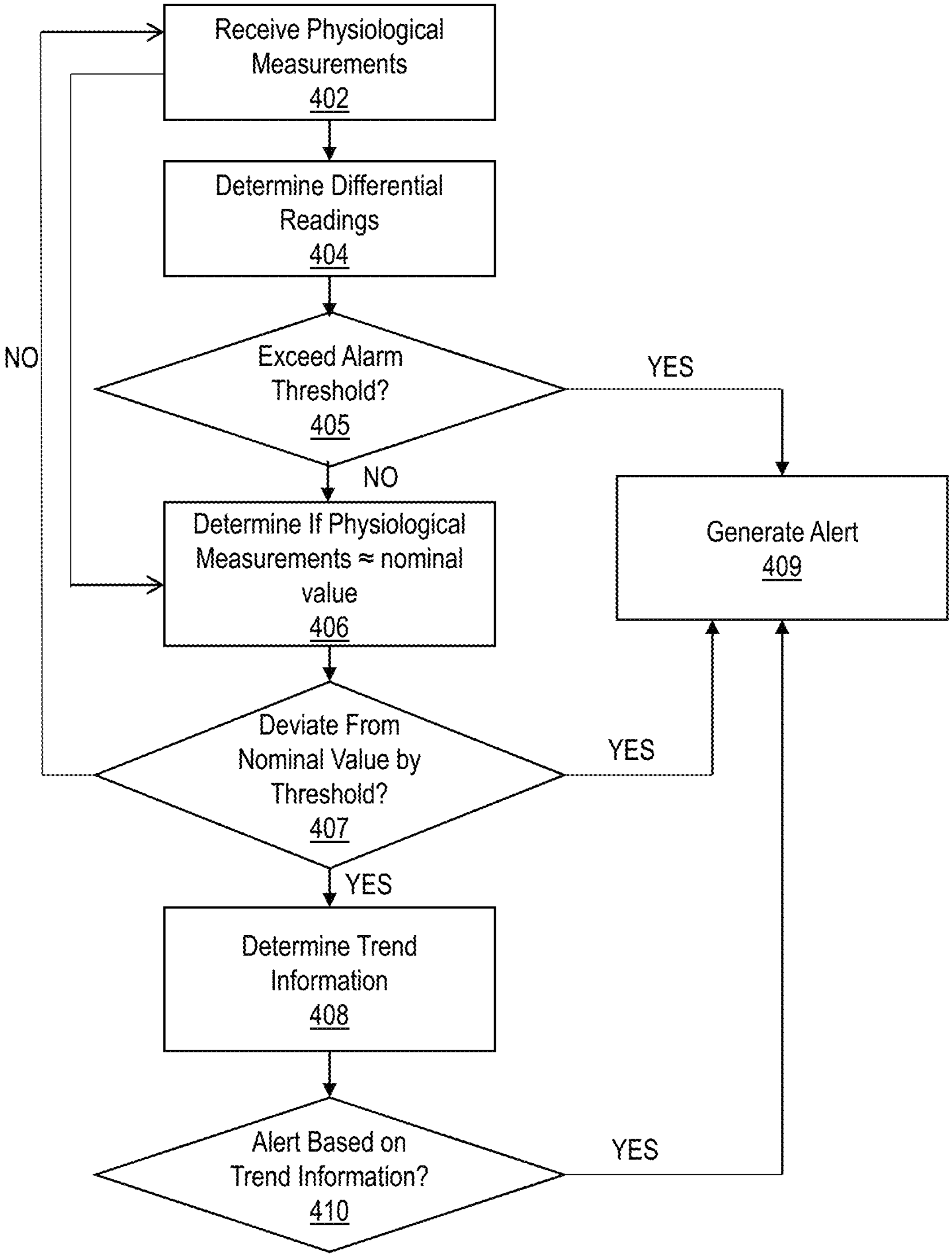
FIG. 4 shows a flowchart of a method for monitoring the health of a patient, according to one or more implementations of the present disclosure.

FIG. 4 shows a flowchart of a method 400 for monitoring the health of a patient, according to one or more implementations of the present disclosure. For illustrative purposes, the method 400 is described as being performed by the wearable sensor platform 304, as described previously with reference to FIG. 3A. The method 400 includes one or more of: receiving physiological measurements (block 402), determining differential readings (block 404); determining if the differential readings exceed an alarm threshold (block 405); determining if physiological measurements approximately equal a nominal value (block 406); determining if the physiological measurements deviate from the nominal value by a threshold value (block 407); determining trend information (block 408); determining whether to generate an alert based on the trend information (block 410); and generating an alert (block 409), which may include displaying the alert on an appropriate display, as further discussed herein.

At block 402, data representing physiological measurements captured at different sensor locations of the wearable sensor platform 304 are received by the analog front end 314.

At block 404, the analog front end 314 provides normalized raw data to the AI machine learning system 340 to determine differential readings between the different sensor locations based on the physiological measurements. The analog front end incorporates mutual distances between the sensor locations and distances between the access point 306 and the sensor locations with the physiological measurements to determine the differential readings between the different sensor locations.

At block 405, in some implementations, the analog front end 314, in conjunction with the AI machine learning system 340, determines whether the differential readings exceed an alarm threshold. The alarm threshold can be determined by the machine learning model 340*a* based on information learned about the user of the wearable sensor platform 304. For example, the machine learning model 340*a* can learn a standard baseline reference (sometimes referred to as a static threshold in this specification) temperature near a fistula (for example, from a plurality of patients) and identify a new threshold for a particular patient based on sensor data collected over time by the wearable sensor platform 304 (sometimes referred to as a dynamic threshold in this specification). The machine learning model 340*a* can then use both the static threshold and the dynamic threshold to identify undesired states near the fistula. If, for example, an alarm threshold is exceeded, then at block 409, the security enforcer 323 generates an alarm. Generating an alarm can include causing the display 320 to exhibit visual cues (e.g., blinking lights) and/or acoustical cues (e.g., beeping sounds). Generating an alarm can include alerting an external systems/devices, such as the dialysis system 360, a mobile device of a physician, or a mobile device of the user of the wearable sensor platform 304.

At block 406, the analog front end 314 determines whether the physiological measurements approximate a nominal value. In some implementations, the physiological measurements approximate the nominal value when the physiological measurements are within a deviation percentage of 1% of the nominal value. In some implementations, the nominal value and the deviation percentage is determined by the machine learning model 340*a* based on information learned about the patient. A state where the physiological measurements approximate the nominal value may be referred to as an equilibrium state.

At block 407, the analog front end 314 determines whether the physiological measurements deviate from the nominal value by a threshold. The threshold can be determined by the machine learning model 340*a* based on information learned about the patient. In some implementations, if the analog front end 314 and the AI machine learning system 340 determine that the physiological measurements deviate from the nominal value by a threshold, then at block 309, the security enforcer 323 generates an alarm, as discussed previously.

In some implementations, at block 408, if the physiological measurements deviate from the nominal value by the threshold, the analog front end 314 and the AI machine learning system 340 determine trend information of the physiological measurements. Trend information includes tracking the physiological measurements for a specified time period to determine whether the physiological measurements are steady, are rising, or are falling. A state where trend information is determined can be called a caution state. The specified time period can be determined by the machine learning model 340*a* based on information learned about the user. In some implementations, the on/off sampling rate of a sensor is based on rates of change (and trend/variance results from the AI machine learning system 340) in data within a defined time window, power management rules and constraints (e.g., due to the wearable nature of the platform 304).

At 410, the analog front end 314 determines whether to generate an alert based on the trend information. For example, if the trend information shows certain measurements rising faster than a threshold rate of change, then the security enforcer 323 can generate an alert. The threshold rates of change can be user specific and determined by the machine learning model 340*a* based on information learned about the user.

As illustrated in FIG. 4, in some implementations, the analog front end 314 can receive physiological measurements at block 402 and then proceed to block 406 to determine whether the physiological measurements approximately equate the nominal value.

Figure 5:
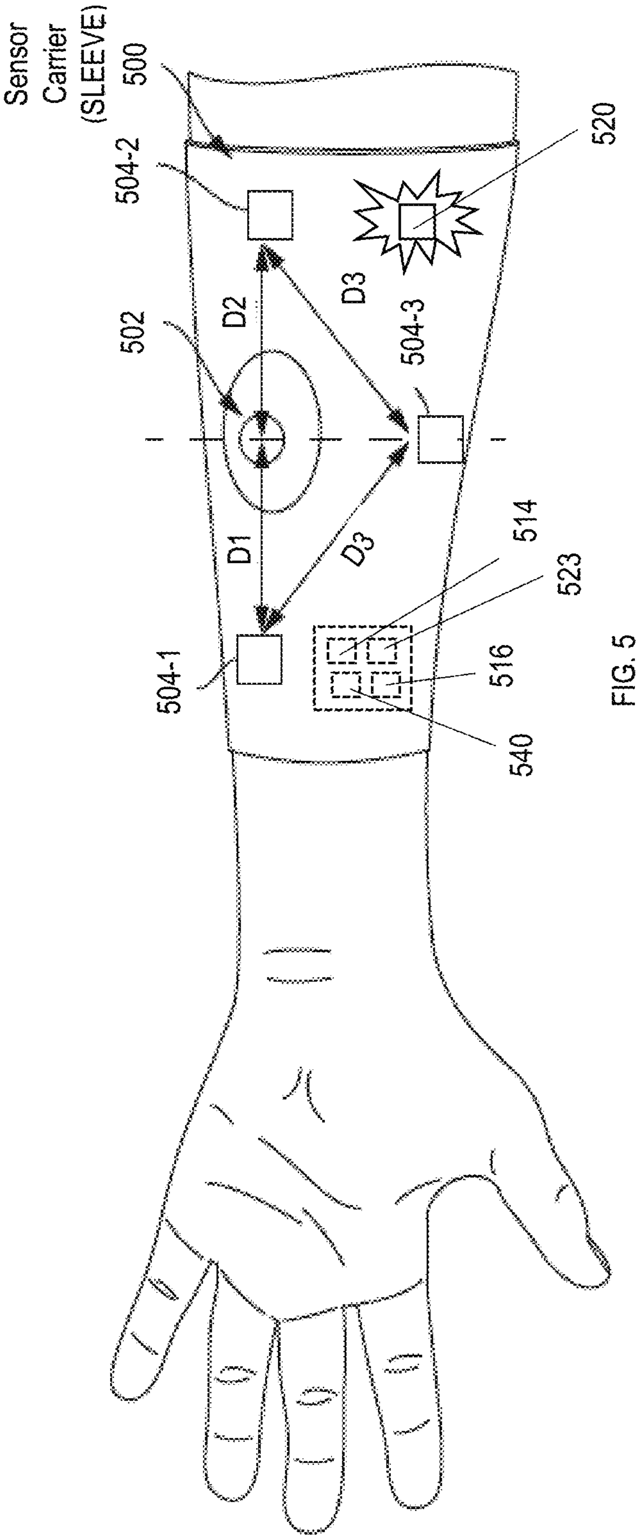
FIG. 5 shows a secure AI enabled wearable sensor platform having temperature sensors for differential temperature measurements, according to one or more implementations of the present disclosure.

FIG. 5 shows a secure AI enabled wearable sensor platform 500, implemented as a sleeve worn on an arm of a patient, having temperature sensors for differential temperature measurements, according to one or more implementations of the present disclosure. In some implementations, the wearable sensor platform 304 discussed previously with reference to FIG. 3A includes some or all aspects of the wearable sensor platform 500. The wearable sensor platform 500 includes an analog front end 514, a security enforcer 523, a processor 516, a machine learning system 540, and a display 520, which can be substantially similar to corresponding components of the wearable sensor platform 304 discussed previously with reference to FIG. 3A.

The wearable sensor platform 500 includes a first temperature sensor 504-1, a second temperature sensor 504-2, and a third temperature sensor 504-3, each placed at different locations from an access point 502 and communicatively coupled to the analog front end 514. In some implementations, the first temperature sensor 504-1 and the second temperature sensor 504-2 are placed at opposite directions from the access point 502. In the illustrated example, the access point 502 is located on one side of the arm, and the third temperature sensor 504-3 is located on the opposite side of the arm. The third temperature sensor 504-3 location is chosen to be as far away from the access point 502 but equidistant to the first and second sensors 504-1, 504-2.

The spatial distance from the access point 502 to the first temperature sensor 504-1 is $d_1$. The spatial distance from the access point 502 to the second temperature sensor 504-2 is $d_2$. The spatial distance from the first temperature sensor 504-1 to the third temperature sensor 504-3 is $d_3$, and the spatial distance from the second temperature sensor 504-2 to the third temperature sensor 504-3 is also $d_3$.

In some implementations, having three readings from three different locations provides an area equivalent calculation for determining qualities of the access point 502. The different readings at the different locations when combined allow for performing trend analysis, developing standard deviations, and developing temperature data profiles and tracking algorithms. The multiple sensor configuration can provide deterministic and highly-reliable system decisions based on triple-redundant sensor data from two or more sensors. This allows decision based voting where a majority of sensors agreeing can be used as a strong bias towards determining whether a minority of sensors are faulty. In some implementations, the temperature sensors 504-1, 504-2, 504-3 sample body temperature, in degrees Celsius, at their respective locations once every minute.

The wearable sensor platform 500 can be configured to perform the method 400 discussed previously with reference to FIG. 4. For example, at block 402, the temperature sensors 504-1, 504-2, 504-3 can collect sensor data at a predetermined sampling rate (e.g., every minute) and sends the sensor data after a prescribed amount of time to the analog front end 514. The sampling rate can be determined by the AI machine learning system 540 based on information learned about the user, and governed by the security enforcer 523 such that the sampling rate is more particular to the user but stays within a validated/safe state.

At block 404, using the spatial distances $d_1$, $d_2$, and $d_3$, and the temperature measurements in the sensor data of block 402, the analog front end 514 can then determine differential temperature readings between the different sensors as provided in Eqs. 1-3. $d_1$ and $d_2$ can be 3-5 cm from the access point 502.

$$\int_{t.start}^{t.stop}\frac{d(T_1d_1)}{dt}-\int_{t.start}^{t.stop}\frac{d(T_2d_2)}{dt} \qquad \text{Eq. 1}$$

$$\int_{t.start}^{t.stop}\frac{d(T_1d_1)}{dt}-\int_{t.start}^{t.stop}\frac{d(T_3d_3)}{dt} \qquad \text{Eq. 2}$$

$$\int_{t.start}^{t.stop}\frac{d(T_2d_2)}{dt}-\int_{t.start}^{t.stop}\frac{d(T_3d_3)}{dt} \qquad \text{Eq. 3}$$

Eq. 1 is the differential temperature reading between the first temperature sensor 504-1 and the second temperature sensor 504-2, where $T_1$ and $T_2$ are temperature measurements from the first and second temperature sensors 504-1, 504-2, respectively. Eq. 2 is the differential temperature reading between the first and third temperature sensors 504-1, 504-3, where $T_3$ is the temperature measurements from the third temperature sensor 504-3. Eq. 3 is the differential temperature reading between the second and third temperature sensors 504-2, 504-3. $T_1$, $T_2$ and $T_3$ are temperature measurements over a time period (t.stop–t.start). Thus, Eqs. 1-3 find the difference between average temperature readings of the first and second temperature sensors 504-1, 504-2, the first and third temperature sensors 504-1, 504-3, and the second and third temperature sensors 504-2, 504-3, respectively.

From the temperature measurements $T_1$, $T_2$ and $T_3$ and the differential temperature readings of Eqs. 1-3, at block 406, the analog front end 514 determines whether each temperature measurement approximates a nominal temperature $T_{nom}$. In some implementations, temperature measurements $T_1$, $T_2$ and $T_3$ should be within a deviation percentage of 1% of the nominal temperature $T_{nom}$. However, the deviation percentage can be determined by the machine learning system 540 as described previously. In the illustrated implementations, when $T_1$, $T_2$ and $T_3$ are within 1% of $T_{nom}$, the wearable sensor platform 500 maintains an equilibrium state. When any of $T_1$, $T_2$ or $T_3$ is not within 1% of $T_{nom}$, the wearable sensor platform 500 transitions to a caution state. The caution state signifies that the body temperature is either too high or too low. As described previously, $T_{nom}$ can be determined by the machine learning system 540 based on information learned about the user.

In some implementations, at block 405, the differential temperature readings of Eqs. 1-3 can be used to determine whether the differential temperature readings exceed an alarm threshold. As discussed previously, the alarm threshold $T_{alarm}$, can be determined by the machine learning system 540 based on information learned about the user. In some implementations, when Eq. 1, 2 or 3 is nonzero and the magnitude of Eq. 1, 2 or 3 evaluated exceeds an alarm threshold $T_{alarm}$, then an alarm is generated at block 409. Eq. 4 summarizes this condition.

$$\text{When}\left(\int_{t.start}^{t.stop}\frac{d(T_1d_1)}{dt} > \int_{t.start}^{t.stop}\frac{d(T_2d_2)}{dt}\ \text{or}\ \int_{t.start}^{t.stop}\frac{d(T_1d_1)}{dt} < \int_{t.start}^{t.stop}\frac{d(T_2d_2)}{dt}\right) \qquad \text{Eq. 4}$$

-continued $$\text{and}\left|\left(\int_{t.start}^{t.stop}\frac{d(T_1d_1)}{dt}-\int_{t.start}^{t.stop}\frac{d(T_2d_2)}{dt}\right)\right| > T_{alarm}$$

OR $$\text{When}\left(\int_{t.start}^{t.stop}\frac{d(T_1d_1)}{dt} > \int_{t.start}^{t.stop}\frac{d(T_3d_3)}{dt}\ \text{or}\ \int_{t.start}^{t.stop}\frac{d(T_1d_1)}{dt} < \int_{t.start}^{t.stop}\frac{d(T_3d_3)}{dt}\right)$$

$$\text{and}\left|\left(\int_{t.start}^{t.stop}\frac{d(T_1d_1)}{dt}-\int_{t.start}^{t.stop}\frac{d(T_3d_3)}{dt}\right)\right| > T_{alarm}$$

OR $$\text{When}\left(\int_{t.start}^{t.stop}\frac{d(T_2d_2)}{dt} > \int_{t.start}^{t.stop}\frac{d(T_3d_3)}{dt}\ \text{or}\ \int_{t.start}^{t.stop}\frac{d(T_2d_2)}{dt} < \int_{t.start}^{t.stop}\frac{d(T_3d_3)}{dt}\right)$$

$$\text{and}\left|\left(\int_{t.start}^{t.stop}\frac{d(T_2d_2)}{dt}-\int_{t.start}^{t.stop}\frac{d(T_3d_3)}{dt}\right)\right| > T_{alarm}$$

In Eqs. 1-4, the following definitions apply:

$T_{alarm}$ is $T_{nom}\times 1\%$ $T_{nom}$ is normal body temperature computed within 24 hours and can be determined by the machine learning system 540 as described previously.

Measurements $T_1$, $T_2$ and $T_3$ made with the temperature sensors provide values for body temperature $T_{body}$ that can be used to determine a body temperature trend bandwidth $T_{body}\pm\delta T$.

At block 408, the client device determines trend information using the temperature measurements if the physiological measurements are determined at block 407 to deviate from $T_{nom}$ by more than 1%. In the event that the wearable sensor platform 500 transitions to a caution state, the temperature sensors 504-1, 504-2, 504-3 will change their sampling rates of temperature measurements $T_1$, $T_2$ and $T_3$ from a slower sampling rate to a faster sampling rate. For example, the sampling rate can change from one temperature measurement per minute to one temperature measurement per second. This faster sampling rate is maintained for a predefined period (e.g., maintained for 5 to 30 minutes). The faster sampling rate and predefined period can be determined by the machine learning system 540 based on information learned about the user (for example, baseline biological reference data, such as blood flow rates). The determined sampling rates and predefined period can be governed by the security enforcer 523 such that the rates/periods stay within a validated/safe state. The temperature measurements obtained during this predefined period are used to determine a temperature trend $T_{trend}$.

In some implementations, when using average temperatures, a faster sampling rate also shortens the averaging time. For example, if sampling at one temperature measurement per second, then average temperatures can be obtained for every 30 seconds, thus the temperature trend $T_{trend}$ is determined with average temperature values obtained every 30 seconds for a 5 to 30 minute period. The temperature trend $T_{trend}$ is a relationship describing change in the different temperature values obtained every 30 seconds.

At block 410, the analog front end 514 analyzes $T_{trend}$ to determine whether to generate an alert. For example, when $T_{trend}$ indicates steady temperature levels and body temperature is greater than $T_{nom}+T_{nom}\times 1\%$, then the analog front end 514 can send a message to the security enforcer 523. The security enforcer 523 can then generate an alert (block 409)

by, for example, sending a message to a clinic treating the user and/or activating the display 520. When $T_{trend}$ indicates rising temperatures during the predefined period (e.g., 5 minutes or 30 minutes) and body temperature is greater than $T_{nom}+T_{nom}\times1\%$, then the security enforcer 523 can generate an alert. When $T_{trend}$ indicates falling temperatures and body temperature is less than $T_{nom}-T_{nom}\times1\%$, then the security enforcer 523 can generate an alert.

The following example certain aspects of the method 400 as previously described with respect to the wearable sensor platform 500 of FIG. 5. The distances $d_1$, $d_2$, and $d_3$ are constants from the view of the placements of temperature sensors 504-1, 504-2, 504-3. Algorithms applied to temperature readings from the temperature sensors 504-1, 504-2, 504-3 therefore account for variables of T (temperature) and t (time).

For example, $t=t_{start}$ is an arbitrary starting value (in time) where temperature T is sampled, and $t=t_{stop}$ is a time where sampling of temperature T is finished. Each temperature sensor 504-1, 504-2, 504-3 continuously reads from $t_{start}$ to $t_{stop}$, and the resulting temperature reading is the integration of T from $t_{start}$ to $t_{stop}$ In some implementations, for saving power, the difference between $t_{start}$ and $t_{stop}$ is small or configurable/adjustable. For example, the duration $t_{start}-t_{stop}$ can be 1 millisecond. A period of no measurements can then ensue. Afterward, the temperature sensors 504-1, 504-2, 504-3 repeat sampling temperature T for another time duration (e.g., $t_{start2}-t_{stop2}=1$ ms).

In some implementations, two temperature readings are taken between $t_{start}$ and $t_{stop}$. For example, when the duration is a 1 ms duration, a temperature measurement T1 is made at $t_{start}$ and a temperature measurement T1.1 is made at $t_{stop}$. From T1 and T1.1, different cases can be used to determine whether the patient has an infection or elevated body temperature. Two cases are described with respect to the T1 and T1.1 measurements:

Case 1: T1−T1.1=0

Case 1 implies that T1 is equal to T1.1, thus there is no change in temperature during the 1 ms duration. Either T1 or T1.1 is compared against normal human body temperature (baselined as the normal body temperature of the patient). If either T1 or T1.1 is over 1% higher than the normal body temperature, then the patient can be deemed to have a fever.

Case 2: T1>T1.1 or T1<T1.1

Case 2 implies that there is a temperature gradient or a local heat source which signals a possibility of an infection or some kind of an anomaly. Depending on the sensor being used, the distance $d_x$ can be used to interpret location of the heat source. For example, when the first temperature sensor 504-1 is placed closer to the access point 502, then elevated temperatures measured at the first temperature sensor 504-1 indicate that the infection is close to the first temperature sensor 504-1. When there is an infection, the human body reacts and elevates body temperature near the location of the infection. Since in FIG. 5 there are three temperature sensors 504-1, 504-2, 504-3 at different distances from the access point 502, an algorithm can be used to combine temperature readings from the different temperature sensors 504-1, 504-2, 504-3 to obtain a more deterministic output (independent of the ambient temperature, and the reading uncertainty from a single temperature sensor).

The previous example showed use of two measurement points in a 1 ms duration. In some embodiments, $t_{start}-t_{stop}$ is long enough to obtain more than two temperature measurements, so each temperature measured can be stored in memory and used for further analysis. The integral functions will begin to look like a simplified form of the Stokes equation and the Fundamental theorem of Calculus.

In some implementations of the method 400 of FIG. 4, using the exemplary configuration of sensors illustrated in FIG. 5, temperature readings from the sensors 3504-1, 504-2, 504-3 are sampled to provide data points, T1, T2, and T3, respectively. Sampling frequency (e.g., sensor on/off duty cycle and sensor sequencing rate) may be dependent on power consumption, battery life, and machine learning. The following discussion uses the first temperature sensor 504-1 as an example, but similar measurements and analyses may be performed in tandem at the second and third temperature sensors 504-2, 504-3.

For example, at block 402, the first temperature sensor 504-1 samples a first reading of T1. The first reading can be a single read, i.e., a single sample, or can be a multiple read, e.g., an average of three fast samples for eliminating body/ambient noise. A multiple read and a single read both provide a single value for the first reading. Design and validation of several algorithms (including baseline references, safety limits, safe operating conditions/constraints, baseline reference rate of change for any sensor reading that can be an indicator for unsafe health conditions) can be completed at a master design and test platform. Each set of sensor algorithms can have two distinct operational functional groups. One groups can use the baseline reference data and AI machined learned data (corresponding rule/goals). The other group can be used to learn and create (for example, using the AI machine learning system) psychological profile for each patient.

At block 406, the first reading is then compared to a nominal body temperature.

At block 407, if the first reading is greater than the nominal body temperature, then at block 408, T1 is sampled for a longer time to determine a temperature trend. Using the temperature trend, then fever (abnormal temperature) can be determined using a rising, falling, or steady state trend of the temperature trend.

That is, after comparison of the first reading with the nominal body temperature, then the sampling time is increased to obtain more temperature readings so that the temperature trend can be determined. The temperature trend will give a direction of change as well as a rate of change so as to know whether the temperature is increasing, decreasing, or remaining steady during the longer sampling time. The longer sampling time or duration is identified above as the duration $t_{start}-t_{stop}$. The duration can be short to obtain a single T value or long to obtain multiple T values.

At block 410, based on the trend information, an alert can be generated.

Figure 6:
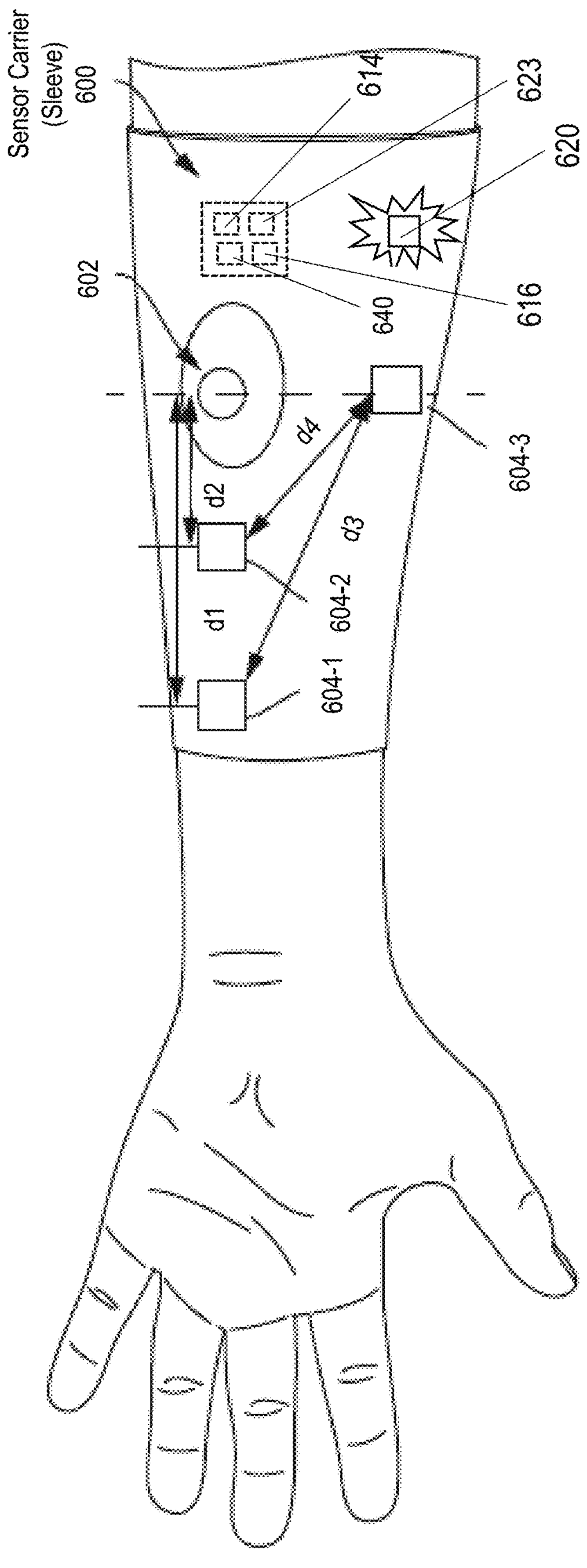
FIG. 6 shows a secure AI enabled wearable sensor platform having temperature sensors for gradient temperature measurements, according to one or more implementations of the present disclosure.

FIG. 6 shows a wearable sensor platform 600 having temperature sensors for gradient temperature measurements, according to one or more implementations of the present disclosure. In some implementations, the wearable sensor platform 304 discussed previously with reference to FIG. 3A includes some or all aspects of the wearable sensor platform 600. The wearable sensor platform 600 includes an analog front end 614, a security enforcer 623, a processor 616, a machine learning system 640, and a display 620, which can be substantially similar to corresponding components of the wearable sensor platform 304 discussed previously with reference to FIG. 3A.

The wearable sensor platform 600 includes a first temperature sensor 604-1, a second temperature sensor 604-2, and a third temperature sensor 604-3, each placed at different locations from an access point 602. In an embodiment, the first and second temperature sensors 604-1, 604-2 are placed at different distances but in a same direction from the access point 602. The access point 602 is located on one side of the arm, and the third temperature sensor 604-3 is located on the opposite side of the arm. For example, anterior compartment placement vs. posterior compartment placement on the forearm. As illustrated in FIG. 6, the placement of the first and second temperature sensors 604-1 and 604-2, can indicate whether there is an infection and help determine a location of the infection.

The spatial distance from the access point 602 to the first temperature sensor 604-1 is $d_1$. The spatial distance from the access point 602 to the second temperature sensor 604-2 is $d_2$. The spatial distance from the first temperature sensor 604-1 to the third temperature sensor 604-3 is $d_3$, and the spatial distance from the second temperature sensor 604-2 to the third temperature sensor 604-3 is $d_4$.

In some implementations, the temperature sensors 604-1, 604-2, 604-3 sample body temperature, in degrees Celsius, at their respective locations once every minute. The wearable sensor platform 600 can perform the method 400 described previously with reference to FIG. 4. For example, the temperature sensors 604-1, 604-2, 604-3 can collect sensor data every minute and sends the sensor data to the analog front end 614 at block 402.

At block 404, differential temperature readings can be determined using the temperature measurements and the spatial distances in a similar manner as described previously with reference to FIG. 5. Differential temperature readings between the first and second temperature sensors 604-1, 604-2 follow Eq. 1, and differential temperature readings between the first and third temperature sensors 604-1, 604-3 follow Eq. 2. Similarly, differential temperature readings between the second and third temperature sensors 604-2, 604-3 are determined by Eq. 5 since distance between the first and third temperature sensors 604-1 and 604-3 and the distance between the second and third temperature sensors 604-2, 604-3 are not equal.

$$\int_{t.start}^{t.stop} \frac{d(T_2 d_2)}{dt} - \int_{t.start}^{t.stop} \frac{d(T_3 d_4)}{dt} \qquad \text{Eq. 5}$$

At block 406, to remain in the equilibrium state, as previously discussed with respect to FIG. 5, temperature measurements $T_1$, $T_2$ and $T_3$ should be, in some implementations, within 1% of the nominal temperature $T_{nom}$. When $T_1$, $T_2$ and $T_3$ are within 1% of $T_{nom}$, the wearable sensor platform 600 maintains the equilibrium state. When any of $T_1$, $T_2$ or $T_3$ is not within 1% of $T_{nom}$, the wearable sensor platform 600 can transition to a caution state. The caution state may signify that the body temperature is too high or too low. As discussed previously with respect to FIG. 5, the temperature measurements $T_1$, $T_2$ and $T_3$ can be average temperature values and not instantaneous measurements.

Similar to the implementation illustrated in FIG. 5, the differential temperature readings can also be used to generate an alarm when Eq. 4 is true. That is, at block 405, if the differential readings exceed an alarm threshold, then at block 409, an alarm is generated. Based on the outcome of block 407, blocks 408 and 410 can be performed in a similar manner where a temperature trend $T_{trend}$ is determined and an alarm is generated using $T_{trend}$ and the body's temperature relative to the normal temperature $T_{nom}$.

Although discussed separately, implementations provided in FIG. 5 and FIG. 6 can be combined to determine both that an infection is present and also a location of the infection. That is, in various embodiments, four or five sensors can be arranged in a wearable sensor platform to obtain both differential and gradient temperature measurements.

Figure 7:
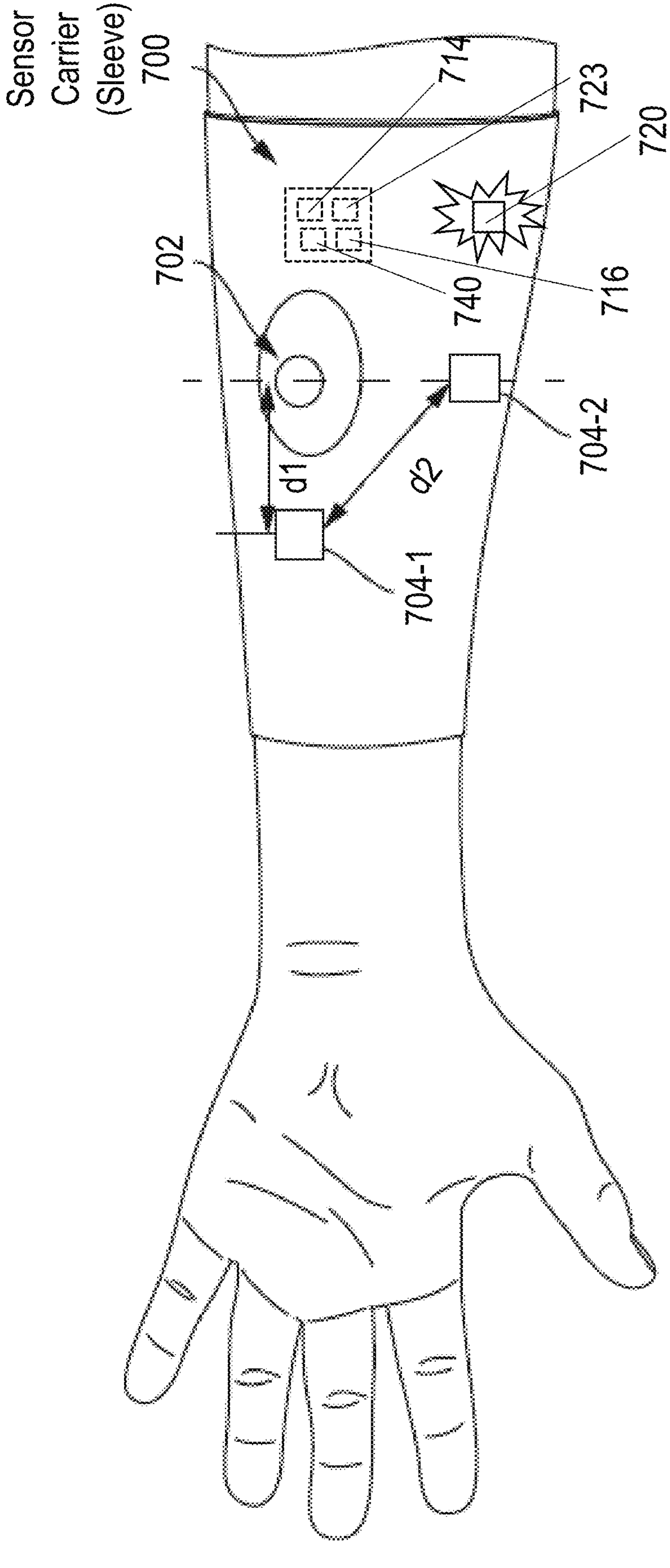
FIG. 7 shows a secure AI enabled wearable sensor platform having pressure sensors, according to one or more implementations of the present disclosure.

FIG. 7 shows a wearable sensor platform 700 having pressure sensors, according to one or more implementations of the present disclosure. In some implementations, the wearable sensor platform 304 discussed previously with reference to FIG. 3A includes some or all aspects of the wearable sensor platform 700. The wearable sensor platform 700 includes an analog front end 714, a security enforcer 723, a processor 716, a machine learning system 740, and a display 720, which can be substantially similar to corresponding components of the wearable sensor platform 304 discussed previously with reference to FIG. 3A.

The wearable sensor platform 700 includes a first pressure sensor 704-1 and a second pressure sensor 704-2, each placed at different locations from an access point 702. The access point 702 is located on one side of the arm, and the second pressure sensor 704-2 is located on the opposite side of the arm. Pressure measurements from the wearable sensor platform 700 can be used to determine whether the access point 702 is at risk of stenosis and/or hematoma. Furthermore, since pressure changes in blood vessels more rapidly than temperature, detection of access point bulging can be performed quickly.

In some implementations, the pressure sensors 704-1, 704-2 are placed above the patient's skin and measures pulsing below the skin. The pulsing can be used to estimate blood vessel pressure once every minute in, e.g., mmHg. The spatial distance from the access point 702 to the first pressure sensor 704-1 is $d_1$. The spatial distance from the first pressure sensor 704-1 to the second pressure sensor 704-2 is $d_2$. In some implementations, the spatial distance $d_2$ is greater than $d_1$.

The wearable sensor platform 700 can perform the method 400 discussed previously with reference to FIG. 4. For example, the pressure sensors 704-1, 704-2 can collect sensor data every minute and send the sensor data to the analog front end 614 client device at block 402.

At block 404, the differential pressure reading between the first pressure sensor 704-1 and the second pressure sensor 704-2 is determined via Eq. 6, where $P_1$ and $P_2$ are pressure measurements obtained from the first and second pressure sensors 704-1, 704-2, respectively. In some implementations, average values of $P_1$ and $P_2$ are used in Eq. 6 instead of instantaneous values.

$$\int_{t.start}^{t.stop} \frac{d(P_1 d_1)}{dt} - \int_{t.start}^{t.stop} \frac{d(P_2 d_2)}{dt} \qquad \text{Eq. 6}$$

The differential pressure reading determined via Eq. 6 can produce different values under a normal state, when a patient is not undergoing dialysis, and under a dialysis state, when the patient is undergoing dialysis. As such, Eq. 6 can be used to obtain differential pressure readings under both the normal state and the dialysis state, and the difference in differential pressure readings between the normal state and the dialysis state can be used to determine whether physiological measurements are approximately within a normal range at block 406.

In a normal state, $P_1=P_2=P_{nom}$, so at block 406, the analog front end 714 determines whether the pressure measurements $P_1$ and $P_2$ approximate a nominal pressure $P_{nom}$. In a dialysis state, $P_1=P_2=P_{dialysis}$, so at block 406, the analog front end 714 determines whether the pressure measurements $P_1$ and $P_2$ approximate a dialysis pressure $P_{dialysis}$. Applying Eq. 6 to pressure measurements obtained in a normal state will provide $diffP_{nom}$, and applying Eq. 6 to pressure measurements obtained in the dialysis state will provide $diffP_{dialysis}$. The difference between $diffP_{nom}$ and $diffP_{dialysis}$ is $diffP_{n-d}$. In some implementations, $diffP_{n-d}$ is bounded by a factor $\delta P_{n-d}$, where $\delta P_{n-d}$ is unique to each person and the state of the fistula or access point 702 computed over a larger period (>24 hours) trend analysis.

In some implementations, each of the sensors 704-1, 704-2 can have different nominal pressures. That is, $P_1$ values can be analyzed to determine whether they approximate $$P^1_{nom},$$

and $P_2$ values can be analyzed to determine whether they approximate $$P^2_{nom}.$$

Each of $$P^1_{nom} \text{ and } P^2_{nom}$$

can have a deviation $\delta P_{nom}$ which can set a bounds for "approximately" as previously used in comparison. $\delta P_{nom}$ is unique to each person and the state of the fistula or access point 702 computed over a larger period (e.g., >24 hours) trend analysis. When $P_1$ is within 1% of $$P^1_{nom}$$

and when $P_2$ is within 1% of $$P^2_{nom},$$

then the wearable sensor platform 700 maintains an equilibrium state. When any of these is untrue, then the wearable sensor platform 700 transitions to a caution state. The caution state signifies that one or more body pressure measurements is too high or too low. 1% is used in the illustrated implementation, but other percentage deviations from nominal pressure can be used as limits, and determined by the machine learning system 740 based on information learned about the user.

At block 405, the differential pressure readings of Eq. 6 can be used to determine whether to generate an alarm. In some implementations, when Eq. 6 is nonzero and the magnitude of Eq. 6 evaluated exceeds an alarm threshold, then an alarm is generated at block 409. Note that since each pressure sensor may have its own nominal value, $$P^1_{nom} \text{ or } P^2_{nom},$$

there can be two alarm thresholds to consider $$P^1_{alarm} \text{ and } P^2_{alarm}.$$

Eq. 7 summarizes conditions for generating an alarm.

$$\text{When } \left(\int_{t.start}^{t.stop}\frac{d(P_1d_1)}{dt} > \int_{t.start}^{t.stop}\frac{d(P_2d_2)}{dt} \text{ or } \int_{t.start}^{t.stop}\frac{d(P_1d_1)}{dt} < \int_{t.start}^{t.stop}\frac{d(P_2d_2)}{dt}\right) \text{ and } \left|\left(\int_{t.start}^{t.stop}\frac{d(P_1d_1)}{dt} - \int_{t.start}^{t.stop}\frac{d(P_2d_2)}{dt}\right)\right| > \quad \text{Eq. 7}$$

In Eq. 7, the following definitions apply:

$P_{alarm}$ is either $$P^1_{alarm} \text{ or } P^2_{alarm}$$

depending on which sensor's measurements are being considered;

$$P^1_{alarm} = P^1_{nom} \times 1\%;$$

$$P^2_{alarm} = P^2_{nom} \times 1\%;$$

$$P^1_{nom}$$

in is normal body pressure near fistula, computed within 24 hours pressure trend analysis;

$$P^2_{nom}$$

in is normal body pressure near fistula, computed within 24 hours pressure trend analysis Measurements $P_1$ and $P_2$ made with pressure sensors provide values for pressure at specific sites and can be used to determine a body pressure trend bandwidth which is defined as $P_{1\ or\ 2} \pm \delta P_{1\ or\ 2}$, where $\pm\delta P_{1\ or\ 2}$ is unique to each person, computed over a larger period (e.g., >24 hours).

At block 408, the analog front end 714 determines trend information using the pressure measurements if the physiological measurements are determined at block 407 to deviate from $$P^1_{nom} \text{ or } P^2_{nom}$$

by more than 1%. In the event that the wearable sensor platform 700 transitions to a caution state, the pressure sensors 704-1, 704-2 will change their sampling rates for pressure measurements $P_1$ and $P_2$ from a slower sampling rate to a faster sampling rate. For example, the sampling rate can change from one pressure measurement per minute to one pressure measurement per second. The faster sampling rate is maintained for a predefined period of time (e.g., maintained for 5 minutes). As discussed previously, the sampling rates and period of time can be determined by the machine learning system 740 based on information learned about the user, and controlled by the security enforcer 723 such that they do not operate outside of a validated/safe state. The pressure measurements obtained during this pre-defined period of time are used to determine pressure trends $$P^1_{trend} \text{ and } P^2_{trend}.$$

At block 410, the analog front end 714 analyzes each of $$P^1_{trend} \text{ and } P^2_{trend}$$

to determine whether to generate an alert. Each of $$P^1_{trend} \text{ and } P^2_{trend}$$

will be referred to as $P_{trend}$ and each of $$P^1_{nom} \text{ and } P^2_{nom}$$

will be referred to as $P_{nom}$ for the following description. Superscripts can be added to obtain trend analysis for each pressure sensor's measurement. When $P_{trend}$ indicates steady pressure levels and body pressure is greater than $P_{nom}+P_{nom}\times 1\%$, then the security enforcer 723 generates an alert. When $P_{trend}$ indicates rising pressure levels during the pre-defined period of time and body pressure is greater than $P_{nom}+P_{nom}\times 1\%$, then security enforcer 723 generates an alert. When $P_{trend}$ indicates falling pressure levels and body pressure is less than $P_{nom}-P_{nom}\times 1\%$, then the security enforcer 723 generates an alert.

Although the implementation illustrated in FIG. 7 includes two pressure sensors, more than two pressure sensors can be included in the wearable sensor platform 700. Placement of sensors can be a combination of that shown for the temperature sensors illustrated in FIGS. 5-6. Multiple sensors being used can provide advantages that were previously described in the temperature sensor setting (e.g., decision based voting, high-reliable system decisions based on triple-redundant sensor data, and so forth).

Furthermore, although a dialysis state with respect to temperature was not described with reference to FIGS. 5-6, in some implementations, temperature measurements during dialysis are also tracked. That is, temperature readings from the temperature sensors can be compared against a $T_{dialysis}$ to determine whether to exit an equilibrium state. Furthermore, a $diffT_{nom}$ and a $diffT_{dialysis}$ can be obtained for each of Eqs. 1-3 during a normal state and during a dialysis state, respectively. Furthermore, a $diffT_{n-d}$ can be defined as $diffT_{nom}-diffT_{dialysis}$. Since the use of measurement metrics in the normal state and the dialysis state is already described above with respect to pressure, similar descriptions are omitted with respect to temperature.

Figure 8:
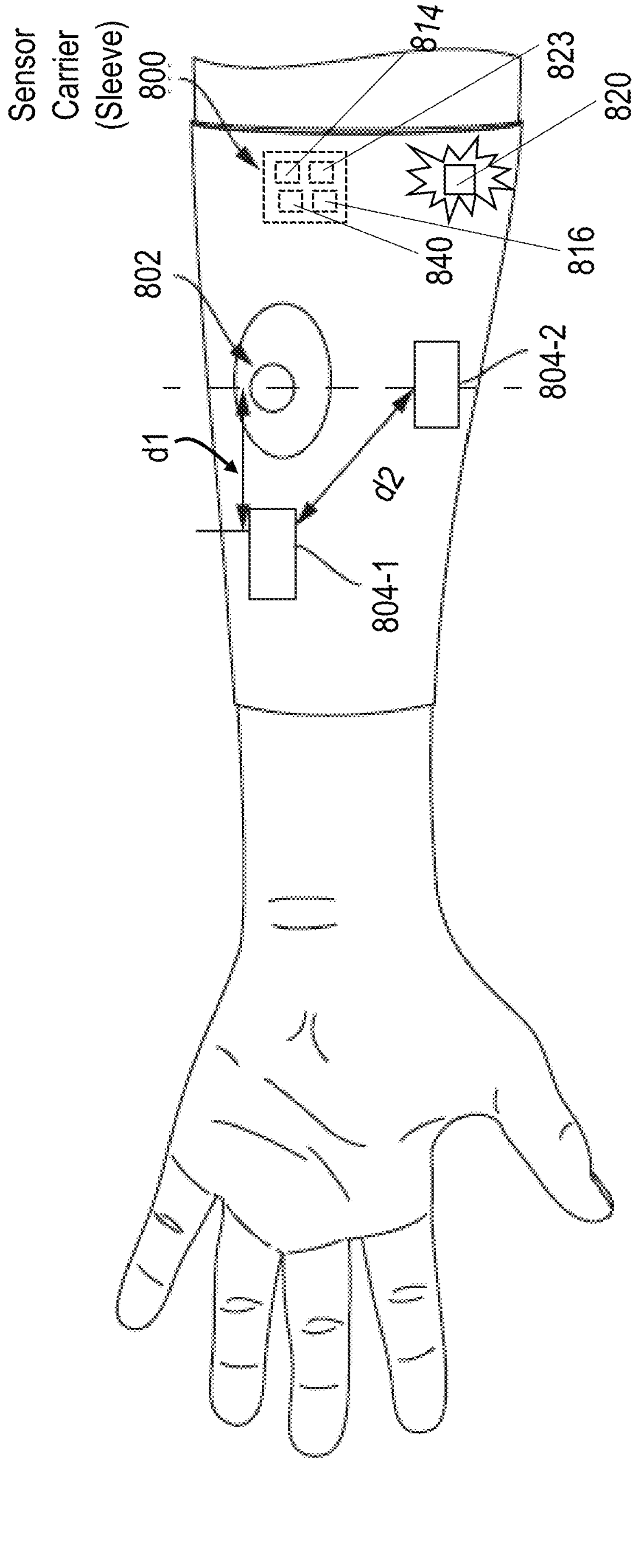
FIG. 8 shows a secure AI enabled wearable sensor platform having spectral sensors, according to one or more implementations of the present disclosure.

FIG. 8 shows a wearable sensor platform 800 having color sensors, according to one or more implementations of the present disclosure. In some implementations, the wearable sensor platform 304 discussed previously with reference to FIG. 3A includes some or all aspects of the wearable sensor platform 800. The wearable sensor platform 800 includes an analog front end 814, a security enforcer 823, a processor 816, a machine learning system 840, and a display 80, which can be substantially similar to corresponding components of the wearable sensor platform 304 discussed previously with reference to FIG. 3A.

The wearable sensor platform 800 includes a first and second color sensor 804-1, 804-2, each being placed at different locations from an access point 802. The access point 802 is located on one side of the arm, and the second color sensor 804-2 is located on the opposite side of the arm. As discussed previously, the color sensors 804-1, 804-2 can be tuned to different frequencies for measuring physiological characteristics of the patient. For example, the color sensors 804-1, 804-2 can include a combination of RGB color sensors, XYZ spectral sensors, and infrared sensors that can facilitate measuring one or more of the following: SpO2, blood CO2 saturation levels, potassium (K) concentration and quantity, Phosphate (PO3) concentration and quantity, possibility of anemia, possibility of fistula infection (e.g., Fistula health, transfer efficiency, and so forth), and other health parameters (e.g., hormone levels). The tuning of each of the color sensors 804-1, 804-2 can be determined by the AI machine learning system 840 and be based on information learned about the patient, as described previously.

For illustrative purposes, the following description of the wearable sensor platform 800 will assume that the color sensors 804-1, 804-2 are tuned for facilitating SpO2 measurements. SpO2 measurements from the wearable sensor platform 800 can be used to check for onset of anemia around the area of the access point 802. SpO2 measurements can also provide information on level of iron deficiency there is in the body.

The spatial distance from the access point 802 to the first color sensor 804-1 is $d_1$. The spatial distance from the first color sensor 804-1 to the second color sensor 804-2 is $d_2$. In some implementations, the spatial distance $d_2$ is greater than $d_1$. The wearable sensor platform 800 can perform the method 400 described previously with reference to FIG. 4. For example, the color sensors 804-1, 804-2 can collect sensor data every minute and send the sensor data after a prescribed amount of time to the analog front end 814.

At block 804, the differential SpO2 reading between the first color sensor 804-1 and the second color sensor 804-2 is determined via Eq. 8, where $SPO2_1$ and $SPO2_2$ are SpO2 measurements obtained from the first and second color sensors 804-1, 804-2, respectively.

$$\int_{t.start}^{t.stop} \frac{d(SPO2_1 d_1)}{dt} - \int_{t.start}^{t.stop} \frac{d(SPO2_2 d_2)}{dt} \quad \text{Eq. 8}$$

The differential SpO2 reading determined via Eq. 8 can produce different values under a normal state, when a patient is not undergoing dialysis, and under a dialysis state, when the patient is undergoing dialysis. As such, Eq. 8 can be used to obtain differential SpO2 readings under both the normal state and the dialysis state, and the difference in differential SpO2 readings between the normal state and the dialysis state can be used to determine whether physiological measurements are approximately within a normal range at block 406.

In a normal state, $SPO2_1=SPO2_2=SPO2_{nom}$, so at block 406, the analog front end 814 determines whether the SpO2 measurements $SPO2_1$ and $SPO2_2$ approximate a nominal blood oxygen saturation $SPO2_{nom}$. In a dialysis state, $SPO2_1=SPO2_2=SPO2_{dialysis}$, so at block 406, the analog front end 814 determines whether the SpO2 measurements $SPO2_1$ and $SPO2_2$ approximate a dialysis blood oxygen saturation $SPO2_{dialysis}$. Applying Eq. 8 to SpO2 measurements obtained in a normal state will provide $diffSPO2_{nom}$, and applying Eq. 8 to SpO2 measurements obtained in the dialysis state will provide $diffSPO2_{dialysis}$. The difference between $diffSPO2_{nom}$ and $diffSPO2_{dialysis}$ is $diffSPO2_{n-d}$. In some implementations, $diffSPO2_{n-d}$ is bounded by a factor $\delta SPO2_{n-d}$, where $\delta SPO2_{n-d}$ is unique to each person and the state of the fistula or access point 802 computed over a larger period (e.g., >24 hours) trend analysis.

In some implementations, there can be different nominal SpO2 values for the color sensors 804-1, 804-2. That is, $SPO2_1$ values are checked to see whether they approximate $$SPO2^1_{nom}$$

and $SPO2_2$ values are checked to see whether they approximate $$SPO2^2_{nom}.$$

Each of $$SPO2^1_{nom} \text{ and } SPO2^2_{nom}$$

can have a deviation of $\delta SPO2_{nom}$ which sets a bounds for “approximately” as used previously in comparison. $\delta SPO2_{nom}$ is unique to each person and the state of the fistula or access point 802 computed over a larger period (e.g., >24 hours) trend analysis. When $SPO2_1$ is within 1% of $$SPO2^1_{nom}$$

and when $SPO2_2$ is within 1% of $$SPO2^2_{nom},$$

then the wearable sensor platform 800 maintains an equilibrium state. When any of these is untrue, then the wearable sensor platform 800 transitions to a caution state. The caution state signifies that one or more body SpO2 measurements is too high or too low. 1% is used as an example here, but other percentage deviations, e.g., 2%, from nominal pressure can be used as limits.

At block 405, the differential SpO2 readings of Eq. 8 can be used to determine whether to generate an alarm. In an embodiment, when Eq. 8 is nonzero and the magnitude of Eq. 8 evaluated exceeds an alarm threshold, then an alarm is generated. Note that since each SpO2 sensor has its own nominal value, $$SPO2^1_{nom} \text{ or } SPO2^2_{nom},$$

there are two alarm thresholds to consider $$SPO2^1_{alarm} \text{ and } SPO2^2_{alarm}.$$

Eq. 9 summarizes conditions for generating an alarm.

$$\text{When } \left(\int_{t.start}^{t.stop} \frac{d(SPO2_1 d_1)}{dt} > \int_{t.start}^{t.stop} \frac{d(SPO2_2 d_2)}{dt} \text{ or } \int_{t.start}^{t.stop} \frac{d(SPO2_1 d_1)}{dt} < \int_{t.start}^{t.stop} \frac{d(SPO2_2 d_2)}{dt}\right) \text{ and } \left|\left(\int_{t.start}^{t.stop} \frac{d(SPO2_1 d_1)}{dt} - \int_{t.start}^{t.stop} \frac{d(SPO2_2 d_2)}{dt}\right)\right| > SPO2_{alarm} \quad \text{Eq. 9}$$

In Eq. 9, the following definitions apply:

$SPO2_{alarm}$ is either $$SPO2^1_{alarm} \text{ or } SPO2^2_{alarm}$$

depending on which sensor's measurements are being considered $$SPO2^1_{alarm} = SPO2^1_{nom} \times 1\%$$

$$SPO2^2_{alarm} = SPO2^2_{nom} \times 1\%$$

$$SPO2^1_{nom}$$

is normal body SpO2 level near fistula, computed within 24 hours SpO2 trend analysis $$SPO2^2_{nom}$$

is normal body SpO2 level near fistula, computed within 24 hours SpO2 trend analysis Measurements $SPO2_1$ and $SPO2_2$ made with color sensors provide values for blood oxygen saturation levels at specific sites and can be used to determine a body SpO2 trend bandwidth which is defined as $SPO2_{1\ or\ 2} \pm \delta SPO2_{1\ or\ 2}$, where $\pm\delta SPO2_{1\ or\ 2}$ is unique to each person, computed over a larger period (e.g., >24 hours).

At block 408, the analog front end 814 determines trend information using the SpO2 measurements if the physiological measurements are determined at block 407 to deviate from $$SPO2^1_{nom} \text{ and } SPO2^2_{nom}$$

by more than 1%. In the event that the wearable sensor platform 800 transitions to a caution state, the first and second sensors 804-1, 804-2 will change their sampling rates for SpO2 measurements $SPO2_1$ and $SPO2_2$ from a slower sampling rate to a faster sampling rate. For example, the sampling rate can change from one SpO2 measurement per minute to one SpO2 measurement per second. The faster sampling rate is maintained for a predefined period of time (e.g., maintained for 5 to 30 minutes). The SpO2 measurements obtained during this predefined period of time are used to determine blood oxygen saturation trends $$SPO2^1_{trend} \text{ and } SPO2^2_{trend}.$$

At block 410, the analog front end 814 analyzes each of $$SPO2^1_{trend} \text{ and } SPO2^2_{trend}$$

to determine whether to generate an alarm. Each of $$SPO2^1_{trend} \text{ and } SPO2^2_{trend}$$

will be referred to as $SPO2_{trend}$ and each of $$SPO2^1_{nom} \text{ and } SPO2^2_{nom}$$

will be referred to as $SPO2_{nom}$ for the following description. Superscripts can be added to obtain trend analysis for each sensor's measurement. When $SPO2_{trend}$ indicates steady SpO2 levels and body SpO2 is greater than $SPO2_{nom}+SPO2_{nom}\times1\%$, then an alarm is generated. When $SPO2_{trend}$ indicates rising SpO2 levels during the predefined period of time and body SpO2 is greater than $SPO2_{nom}+SPO2_{nom}\times1\%$, then an alarm is generated. When $SPO2_{trend}$ indicates falling SpO2 levels and body SpO2 is less than $SPO2_{nom}-SPO2_{nom}\times1\%$, then an alarm is generated.

Although described separately, each of the implementations illustrated in FIGS. 5-8 is combinable with other illustrated implementations. For example, different types of sensors can be provided in a wearable sensor platform to provide information on infection and hematoma using temperature and pressure. Furthermore, other types of sensors like accelerometers and force sensors can be used to determine whether the patient is putting too much weight or is moving an arm too quickly. Information obtained by these sensors can be used to alert emergency contacts so that they can inform the patient on how to better be aware of posture so as to not generate such alerts. Embodiments of the disclosure provide a way of educating patients on proper maintenance of fistulas to combat any lack of awareness of potentially dangerous behavior or improper maintenance on the patient's part.

Implementations of the disclosure can be used to monitor peritoneal dialysis access points or to monitor other surgical grafts. A wearable sensor platform according to some implementations of the disclosure can be provided as a band especially when all sensors are placed on a same side.

In an example, a patient puts on a wearable sensor platform according to implementations of the disclosure. The wearable sensor platform is fitted with sensor straps that prevent the sensors from moving once in place. The system then turns on automatically after the sensor straps are fixed. The sensors provide pressure and temperature data which are used to determine whether the access point being monitored is healthy. A physician/clinic is alerted by the wearable sensor platform if there is an anomaly. In some implementations, the wearable sensor platform is worn during dialysis to inform a physician on how to, for example, adjust blood flow rate of the dialysis machine based on performance of the access point.

Figure 9:
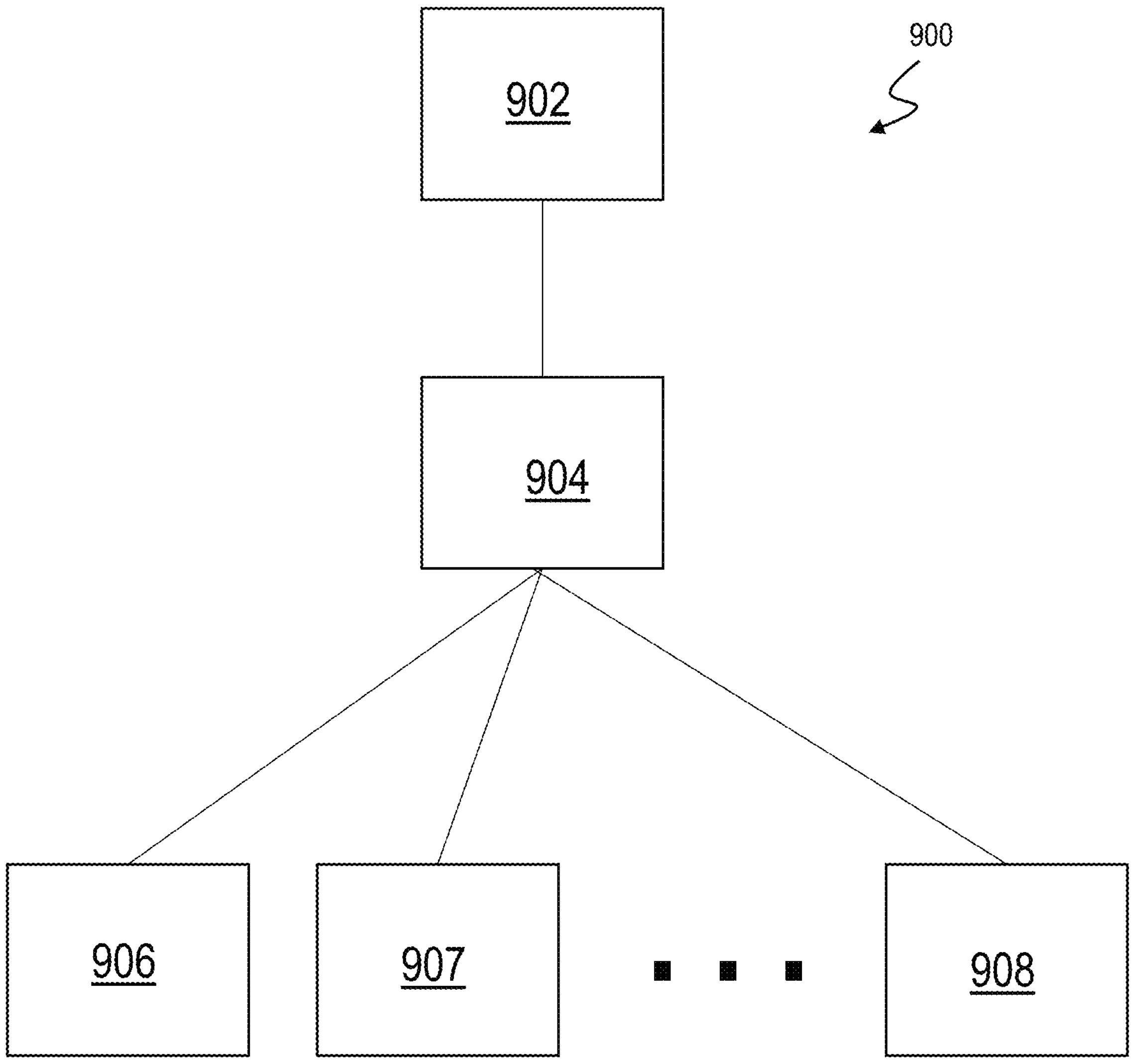
FIG. 9 shows a block diagram of an environment including a factory module, a supervisor module, and a plurality of operations modules, according to one or more implementations of the present disclosure.

FIG. 9 shows a block diagram of an environment 900 including a factory module 902, a supervisor module 904, and a plurality of operations modules 906-908, according to one or more implementations of the present disclosure. The factory module 902 may be provided at a point of manufacture of a wearable sensor platform (such as the platform 304 described previously with reference to FIG. 3A) or a dialysis system (such as the dialysis systems 100, 200, 360 described in this specification). In some implementations, the MDT platform 370 described previously with reference to FIG. 3B includes the factory module 902. The supervisor module 904 is provided on a dialysis system (such as the dialysis systems 100, 200, 360 described in this specification) and the operation modules 906-908 are provided on a wearable sensor platform (such as the platforms 304, 500, 600, 700, 800 described in this specification). In some implementations, the security engine platform 361 described previously with reference to FIG. 3B includes the supervisor module 904, and at least one of the operations modules 906-908 can encompass the security enforcer 323, machine learning system 340, the analog front end 314, and the sensors 312 described previously with reference to FIG. 3A. Each of the operations modules 906-908 can encompass different wearable sensor platforms. As indicated previously, the factory module 902 provides, in a secure and non-repudiable manner, limits/constraints to the supervisor module 904 that the supervisor module 904 uses to provide limits/constraints in a secure and non-repudiable manner to provide for adaptive optimizations/state changes to each of the operation modules 906-908.

The supervisor module 904 constrains adaptive optimizations of the operation modules 906-908 provided by machine learning systems to maintain each of the operation modules 906-908 in a state that is consistent with operating in a safe and effective manner and consistent with prior regulatory approval for each of the modules 906-908. For example, the supervisor module 904 can provide limits/constraints to a security enforcer (such as the security enforcer 323 discussed previously with reference to FIG. 3A) such that it can determine if the state of a particular operation module is acceptable after having been altered using machine learning (e.g., artificial intelligence).

In some implementations, a set of constraints for at least one of the operation modules 906-908 may be determined when a wearable sensor platform is manufactured (or sometime after manufacture in connection with maintenance). In some implementations, different specific units of the same model of wearable sensor platform can use different constraints due to calibration differences and/or different deployment scenarios. The factory module 902 provides constraint data to the supervisor module 904 and provides a cryptographic one-way hash of the constraint data. In some implementations, the cryptographic one-way hash is an SHA256 hash. In some implementations, other appropriate cryptographic one-way hash algorithms are used. The factory module 902 can generate a private/public cryptographic key pair and may provide the public key to the supervisor module 904. In some implementation, the public key may be provided in a digital certificate that is signed by a trusted authority under the X.509 PKI standard. The factory module 902 may then provide to the supervisor module 904 a digital signature of the cryptographic one-way hash of the constraint data. The supervisor module 904 may then verify the source of the digitally-signed cryptographic one-way hash of the constraint data using the public key of the factory module 902 and may then authenticate the received constraint data using the one-way hash value. This mechanism can prevent repudiation of the constraint data since the only possible source is the factory module 902, assuming that the private key has not been disclosed to any party outside the factory module 902. For each of the operation modules 906-908, the factory module 902 can generate a multi-mode encoded key pair, in which the private key is sent to and obtained by the supervisor module 904, and the public key is sent to the supervisor module 904 and transmitted to one of the operation modules 906-908. The multi-mode encoded key pair mechanism can be used by the supervisor module 904 to authenticate data received from each of the operation modules 906-908.

Figure 10:
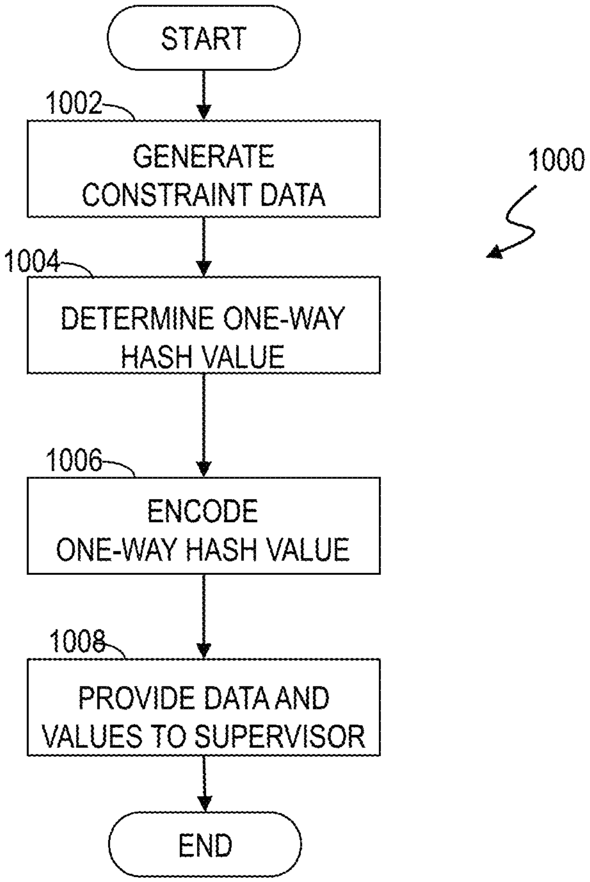
FIG. 10 shows a flowchart of a method performed in connection with transferring calibration and configuration data, baseline reference data, and security keys from a factory module to a supervisor module, according to one or more implementations of the present disclosure.

FIG. 10 shows a block diagram of a method 1000 performed in connection with transferring state constraint data from a factory module to a supervisor module, according to one or more implementations of the present disclosure. In some implementations, the factory module 902 performs the method 1000 in connection with providing the constraint data to the supervisor module 904. The method 1000 includes generating constraint data (block 1002), determining one-way hash value (block 1004), digitally signing one-way hash value (block 1006), and providing data and values to supervisor module (block 1008).

At block 1002, the factory module 902 determines the constraint data. Generally, constraints placed on a particular operation module can be determined based on initial values used for the particular module, as well as a determination of any limits needed for providing safe and effective operations. Some of the constraints may be determined empirically based on clinical/testing experience. Some of the constraints can be based, at least in part, on regulatory considerations, where values of some operational parameters are not allowed to go beyond values used for a particular operation module in connection with previously receiving regulatory approval.

At block 1004, a one-way hash value (e.g., SHA256) of the constraint data is calculated. At block 1006, MDT provides digital signatures from foundation security keys to the factory system, to authenticate and validate a wearable sensor platform. The platform 902 provides a digital signature of the one-way hash value. At block 1008, the factory module 902 provides the supervisor module 904 with the constraint data, the one-way hash value of the constraint data, and the digital signature of the one-way hash value of the constraint data. The method 1000 may be performed when a wearable sensor platform is first manufactured or in connection with subsequent maintenance after the wearable sensor platform has been operational.

As indicated previously, the supervisor module 904 can have a private key and a corresponding public key that may be used for the secure and non-repudiable transfer of data (e.g., constraint data) to the operation modules 906-908. Just as with transfer of data from the factory module 902 to the supervisor module 904, data from the supervisor module 904 may be transferred to each of the operation modules 906-908 by first determining a one-way has of the data (using, for example, the SHA256 one-way cryptographic hash mechanism), digitally signing the one-way hash value, and then transferring the data, the one-way hash value, and the digital signature of the one-way hash value. Similarly, each of the operation modules 906-908 may have a private key and a corresponding public key that may be used to provide a secure and non-repudiable data transfer to the supervisor module 904. For example, each of the operation modules 906-908 may use the key pairing for encrypting raw and processed sensor data, and sending the sensor data to the supervisor module 904. The supervisor module 904 may then authenticate each of the operation modules and the data received from each of the operation module 906-908.

Figure 11A:
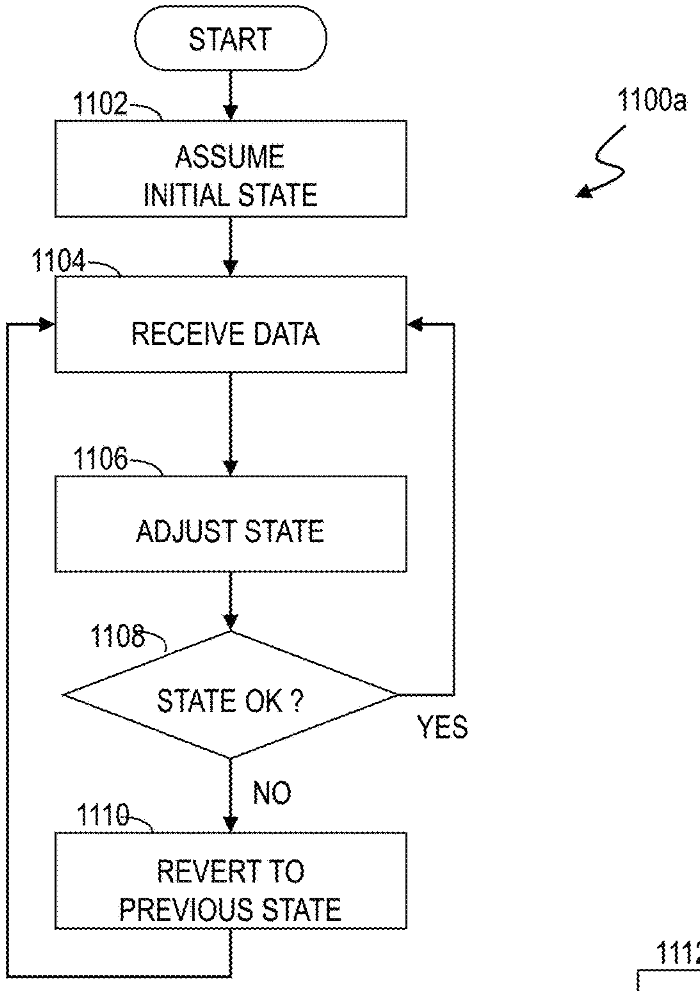
FIG. 11A shows a flowchart of a method performed by an AI-machine learning system in conjunction with a security enforcer, according to one or more implementations of the present disclosure.

FIG. 11A shows a flowchart of a method 1100*a* performed by an AI machine learning system in conjunction with a security enforcer, according to one or more implementations of the present disclosure. For example, as previously indicated, the machine learning systems described in this specification (such as the machine learning system 340 described previously with reference to FIG. 3A) can perform this method in conjunction with the security enforcers described in this specification (such as the security enforcer 323 described previously with reference to FIG. 3A) to provide constrained adaptive optimization of a corresponding wearable sensor platform. Components that may be adapted by the method 1100*a* can include sensor settings (such as the frequency and sampling rates of the sensors described in this specification) and processing algorithms used by analog front ends described in this specification (such as nominal values used in previously described algorithms. In general, any operational aspect of a wearable sensor platform may be adapted using machine learning (artificial intelligence). The method 1100*a* includes assuming an initial state (block 1102), receiving data (block 1104), adjusting a state (block 1106), determining if the state is acceptable (block 1108), and reverting to a previous state (block 1110).

At block 1102, an initial state of a wearable sensor platform is determined. The initial state may be determined at the time of manufacture or may be otherwise input to the system by a supervisor module (discussed in more detail elsewhere herein) or some other external source. For example, the initial state may include an initial value for sensor settings (e.g., an initial sample rate, an initial frequency, and so forth) and/or an initial nominal value (e.g., using a predetermined standard body temperature for as a nominal temperature). In some cases the initial state may be based on the specific operator and/or patient, which may be detected automatically, as described previously.

At block 1104, inputs are provided to the machine learning system. The machine learning system receives appropriate input data for the operations being optimized.

At block 1106 the machine learning system adapts operational parameters/algorithmic parameters according to the input data received. Generally, the specific adaptive optimizations that occur depend upon the input data, the machine learning mechanism that is used (e.g., neural networks), and the specific objective of the machine learning optimizations (e.g., optimize sensor settings).

At block 1108, it is determined if the state of the module is acceptable after the adaptive optimizations have been applied at block 1106. Although adaptive optimizations using artificial intelligence may be useful, it is important that the adaptive optimizations do not cause the system to operate in a way that is potentially unsafe for patients or otherwise detrimental. This is enforced by a security enforcer (such as the security enforcer 323 discussed previously with reference to FIG. 3A), which is discussed previously in more detail.

If it is determined at block 1108 that the new state of the module is not acceptable, then control transfers from block 1108 to block 1110, where the state of the module is restored/reverted to a previous state. The previous state may be either an initial state (i.e., the state set at block 1102, described previously), the state of the module just prior to execution of block 1106, or some other state that is otherwise acceptable. The previous state may be an original validated state. Following block 1110, control transfers back to block 1104 for another iteration. In some implementations, block 1104 also follows directly from block 1108 if it determined that the state of the operation module is acceptable.

Figure 11B:
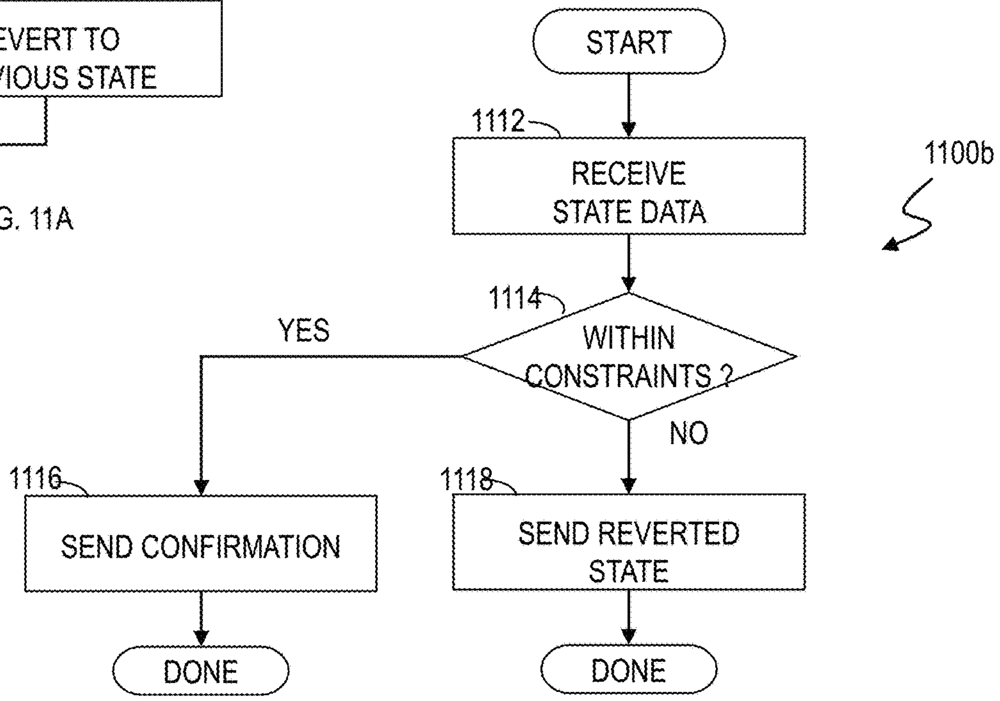
FIG. 11B shows a flowchart of a method performed by a security enforcer in conjunction with an AI-machine learning system, according to one or more implementations of the present disclosure.

FIG. 11B shows a flowchart of a method 1100*b* performed by a security enforcer in conjunction with a machine learning system, according to one or more implementations of the present disclosure. In some implementations, the method 1100*b* is performed by the security enforcers described in this specification (such as the security enforcer 323 described previously with reference to FIG. 3A) in conjunction with performing blocks 1108-1110 of the method 1100*a* discussed previously with reference to FIG. 11A.

The method 1100*b* includes receiving state data (block 1112), determining if the state data is within constraints (block 1114), sending confirmation (block 1116) and sending reverted state (block 1118).

At block 1112, the security enforcer receives state data for the new state of the operation component being tested (such as the sensors, analog front end, and so forth) from the machine learning system.

At block 1114, the security enforcer examines the state data to determine if any of the operational parameters of the new state are outside any constraints that were provided as part of the constraint data previously received from a security engine (such as the security engine 361 discussed previously with reference to FIG. 3B), which, in some implementations, was received by the security engine from an MDT platform (such as the MDT platform 370 discussed previously with reference to FIG. 3B. If none of the new operational parameters are outside any of the constraints, then control transfers from block 1104 to block 1106 where a confirmation is sent from the security enforcer to the machine learning system. Receipt of the confirmation causes the machine learning system to cause the component to begin operating in the new state. If it is determined at block 1104 that at least one of the new operational parameters are outside the constraints, then control transfers from block 1104 to block 1108 where a data for a previous state is sent to the machine learning system, which then causes the component to revert to the previous state.

Figure 12:
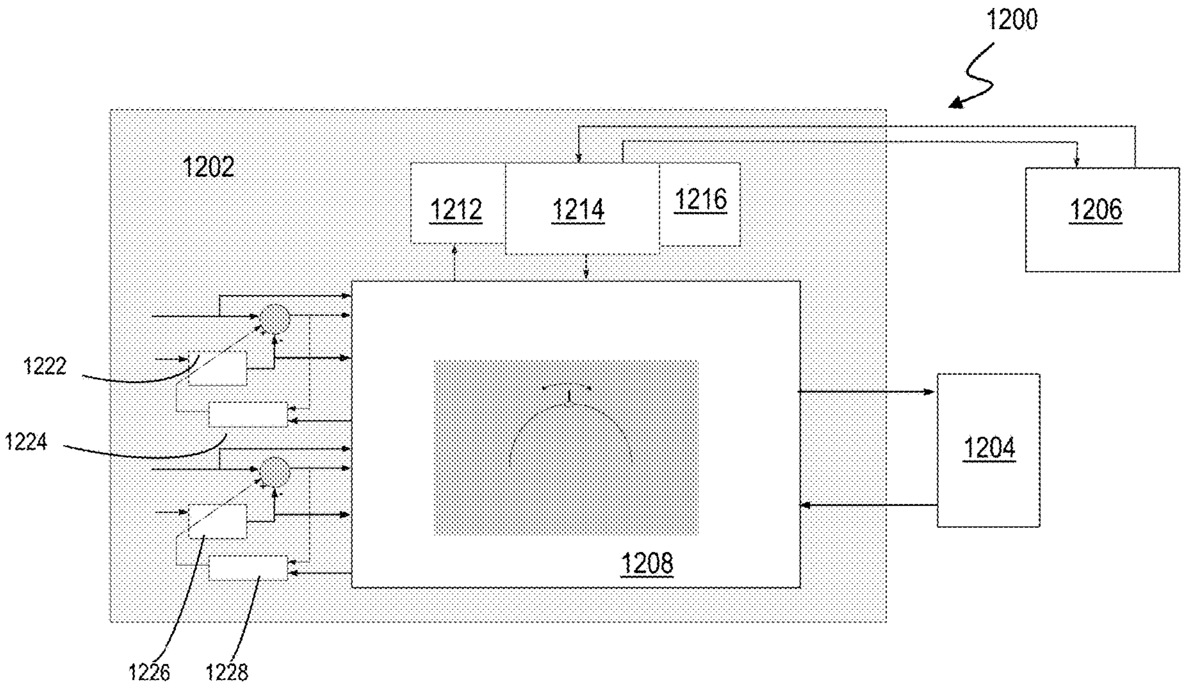
FIG. 12 shows a block diagram of an environment including an AI-machine learning system, a security engine, a dynamic operational data set, and a baseline reference data set, according to one or more implementations of the present disclosure.

FIG. 12 shows a block diagram of an environment 1200 including a wearable sensor platform 1202, a security engine 1206, and a user 1204, according to one or more implementations of the present disclosure. Each of the wearable sensor platforms described in this specification (such as the wearable sensor platform 304 described previously with reference to FIG. 3A) can include the wearable sensor platform 1202. The wearable sensor platform 1202 is coupled to the user 1204 that provides input to the wearable sensor platform 1202 using sensors of the wearable sensor platform 1202. In some situations, the wearable sensor platform 1202 may also be coupled to the security engine 1206 (such as when the patient is undergoing dialysis treatment) that provides baseline data and constraints to a security enforcer 1214 of the wearable sensor platform 1202, as previously described in more detail.

As previously described, the wearable sensor platform 1202 includes an AI machine learning system 1208 that can use one or more artificial intelligence based optimization techniques. The techniques can provide data to a dynamic operational data set 1212 and receive data from the security enforcer 1214. The security enforcers includes mechanisms for constraining critical parameters, as previously described, and may include a control value table, a guard/compliance enforcer, AI specific learning rules, and mechanisms for handling loading and monitoring of dynamic system baseline data. The security enforcer can exchange data with the security engine 1206 when the security engine 1206 is present (for example, using short range wireless communication and secure communications, as described previously). The security enforcer 1214 also receives data from a static operational data set 1216. The static operational data set 1216 includes static (fixed) counterparts for data provided by the dynamic operational data set 1212. In some implementations, both the dynamic operational data set 1212 and the static operational data set 1216 include static and dynamic corresponding data for system specific operating parameters, system calibration data, system configuration data, system alarm limits and safe operating limits, and embedded processor/FPGA boot code. The security engine 1206 provides authentication and facilitates copying data from the static operational data set 1216 to the security enforcer 1214.

The machine learning system 1208 exchange data with a first adaptive control algorithm 1222 and a corresponding first adaptive correction algorithm 1224 and exchange data with a second adaptive control algorithm 1226 and a corresponding second adaptive correction algorithm 1228.

The first adaptive control algorithm 1222 and the first adaptive correction algorithm 1224 may perform this optimization using any one of a number of possible mechanisms, including known optimization mechanisms. However, for safety/regulatory considerations, the machine learning system 1208 is constrained by the security enforcer 1214 to prevent operational parameters from deviating too far from values of the static operational data set 1216. In a similar way, the second adaptive control algorithm 1226 and the corresponding second adaptive correction algorithm 1228 may be used to optimize other operational parameters, such as a sensor's sampling rate.

Figure 13:
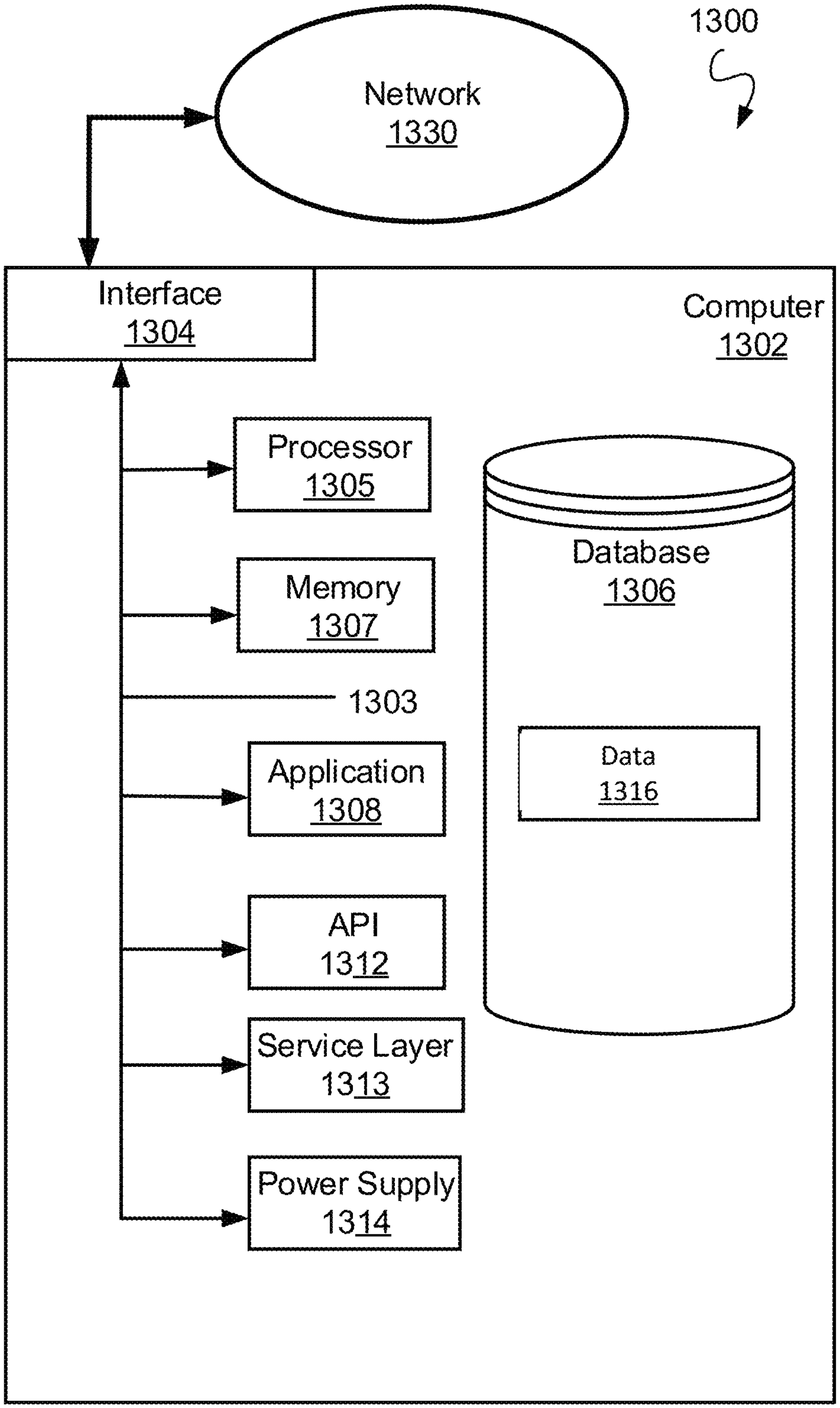
FIG. 13 is a block diagram of an example computer system used to provide computational functionalities associated with described algorithms, methods, functions, processes, flows, and procedures described in the present disclosure.

FIG. 13 is a block diagram of an example computer system 1300 used to provide computational functionalities associated with described algorithms, methods, functions, processes, flows, and procedures described in the present disclosure, according to some implementations of the present disclosure. The illustrated computer 1302 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 1302 can include input devices such as keypads, keyboards, and touch screens that can accept user information. Also, the computer 1302 can include output devices that can convey information associated with the operation of the computer 1302. The information can include digital data, visual data, audio information, or a combination of information. The information can be presented in a graphical user interface (UI) (or GUI).

The computer 1302 can serve in a role as a client, a network component, a server, a database, a persistency, or components of a computer system for performing the subject matter described in the present disclosure. The illustrated computer 1302 is communicably coupled with a network 1330. In some implementations, one or more components of the computer 1302 can be configured to operate within different environments, including cloud-computing-based environments, local environments, global environments, and combinations of environments.

At a high level, the computer 1302 is an electronic computing device operable to receive, transmit, process, store, and manage data and information associated with the described subject matter. According to some implementations, the computer 1302 can also include, or be communicably coupled with, an application server, an email server, a web server, a caching server, a streaming data server, or a combination of servers.

The computer 1302 can receive requests over network 1330 from a client application (for example, executing on another computer 1302). The computer 1302 can respond to the received requests by processing the received requests using software applications. Requests can also be sent to the computer 1302 from internal users (for example, from a command console), external (or third) parties, automated applications, entities, individuals, systems, and computers.

Each of the components of the computer 1302 can communicate using a system bus 1303. In some implementations, any or all of the components of the computer 1302, including hardware or software components, can interface with each other or the interface 1304 (or a combination of both), over the system bus 1303. Interfaces can use an application programming interface (API) 1312, a service layer 1313, or a combination of the API 1312 and service layer 1313. The API 1312 can include specifications for routines, data structures, and object classes. The API 1312 can be either computer-language independent or dependent. The API 1312 can refer to a complete interface, a single function, or a set of APIs.

The service layer 1313 can provide software services to the computer 1302 and other components (whether illustrated or not) that are communicably coupled to the computer 1302. The functionality of the computer 1302 can be accessible for all service consumers using this service layer. Software services, such as those provided by the service layer 1313, can provide reusable, defined functionalities through a defined interface. For example, the interface can be software written in JAVA, C++, or a language providing data in extensible markup language (XML) format, or a design language HDL for FPGA and/or model based design language (such as MathWorks). While illustrated as an integrated component of the computer 1302, in alternative implementations, the API 1312 or the service layer 1313 can be stand-alone components in relation to other components of the computer 1302 and other components communicably coupled to the computer 1302. Moreover, any or all parts of the API 1312 or the service layer 1313 can be implemented as child or sub-modules of another software module, enterprise application, or hardware module without departing from the scope of the present disclosure.

The computer 1302 includes an interface 1304. Although illustrated as a single interface 1304 in FIG. 13, two or more interfaces 1304 can be used according to particular needs, desires, or particular implementations of the computer 1302 and the described functionality. The interface 1304 can be used by the computer 1302 for communicating with other systems that are connected to the network 1330 (whether illustrated or not) in a distributed environment. Generally, the interface 1304 can include, or be implemented using, logic encoded in software or hardware (or a combination of software and hardware) operable to communicate with the network 1330. More specifically, the interface 1304 can include software supporting one or more communication protocols associated with communications. As such, the network 1330 or the interface's hardware can be operable to communicate physical signals within and outside of the illustrated computer 1302.

The computer 1302 includes a processor 1305. Although illustrated as a single processor 1305 in FIG. 13, two or more processors 1305 can be used according to particular needs, desires, or particular implementations of the computer 1302 and the described functionality. Generally, the processor 1305 can execute instructions and can manipulate data to perform the operations of the computer 1302, including operations using algorithms, methods, functions, processes, flows, and procedures as described in the present disclosure.

The computer 1302 also includes a database 1306 that can hold data for the computer 1302 and other components connected to the network 1330 (whether illustrated or not). For example, database 1306 can be an in-memory, conventional, or a database storing data consistent with the present disclosure. In some implementations, database 1306 can be a combination of two or more different database types (for example, hybrid in-memory and conventional databases) according to particular needs, desires, or particular implementations of the computer 1302 and the described functionality. Although illustrated as a single database 1306 in FIG. 13, two or more databases (of the same, different, or combination of types) can be used according to particular needs, desires, or particular implementations of the computer 1302 and the described functionality. While database 1306 is illustrated as an internal component of the computer 1302, in alternative implementations, database 1306 can be external to the computer 1302.

The computer 1302 also includes a memory 1307 that can hold data for the computer 1302 or a combination of components connected to the network 1330 (whether illustrated or not). Memory 1307 can store any data consistent with the present disclosure. In some implementations, memory 1307 can be a combination of two or more different types of memory (for example, a combination of semiconductor and magnetic storage) according to particular needs, desires, or particular implementations of the computer 1302 and the described functionality. Although illustrated as a single memory 1307 in FIG. 13, two or more memories 1307 (of the same, different, or combination of types) can be used according to particular needs, desires, or particular implementations of the computer 1302 and the described functionality. While memory 1307 is illustrated as an internal component of the computer 1302, in alternative implementations, memory 1307 can be external to the computer 1302.

The application 1308 can be an algorithmic software engine providing functionality according to particular needs, desires, or particular implementations of the computer 1302 and the described functionality. For example, application 1308 can serve as one or more components, modules, or applications. Further, although illustrated as a single application 1308, the application 1308 can be implemented as multiple applications 1308 on the computer 1302. In addition, although illustrated as internal to the computer 1302, in alternative implementations, the application 1308 can be external to the computer 1302.

The computer 1302 can also include a power supply 1314. The power supply 1314 can include a rechargeable or non-rechargeable battery that can be configured to be either user- or non-user-replaceable. In some implementations, the power supply 1314 can include power-conversion and management circuits, including recharging, standby, and power management functionalities. In some implementations, the power-supply 1314 can include a power plug to allow the computer 1302 to be plugged into a wall socket or a power source to, for example, power the computer 1302 or recharge a rechargeable battery.

There can be any number of computers 1302 associated with, or external to, a computer system containing computer 1302, with each computer 1302 communicating over network 1330. Further, the terms "client," "user," and other appropriate terminology can be used interchangeably, as appropriate, without departing from the scope of the present disclosure. Moreover, the present disclosure contemplates that many users can use one computer 1302 and one user can use multiple computers 1302.

Figure 14:
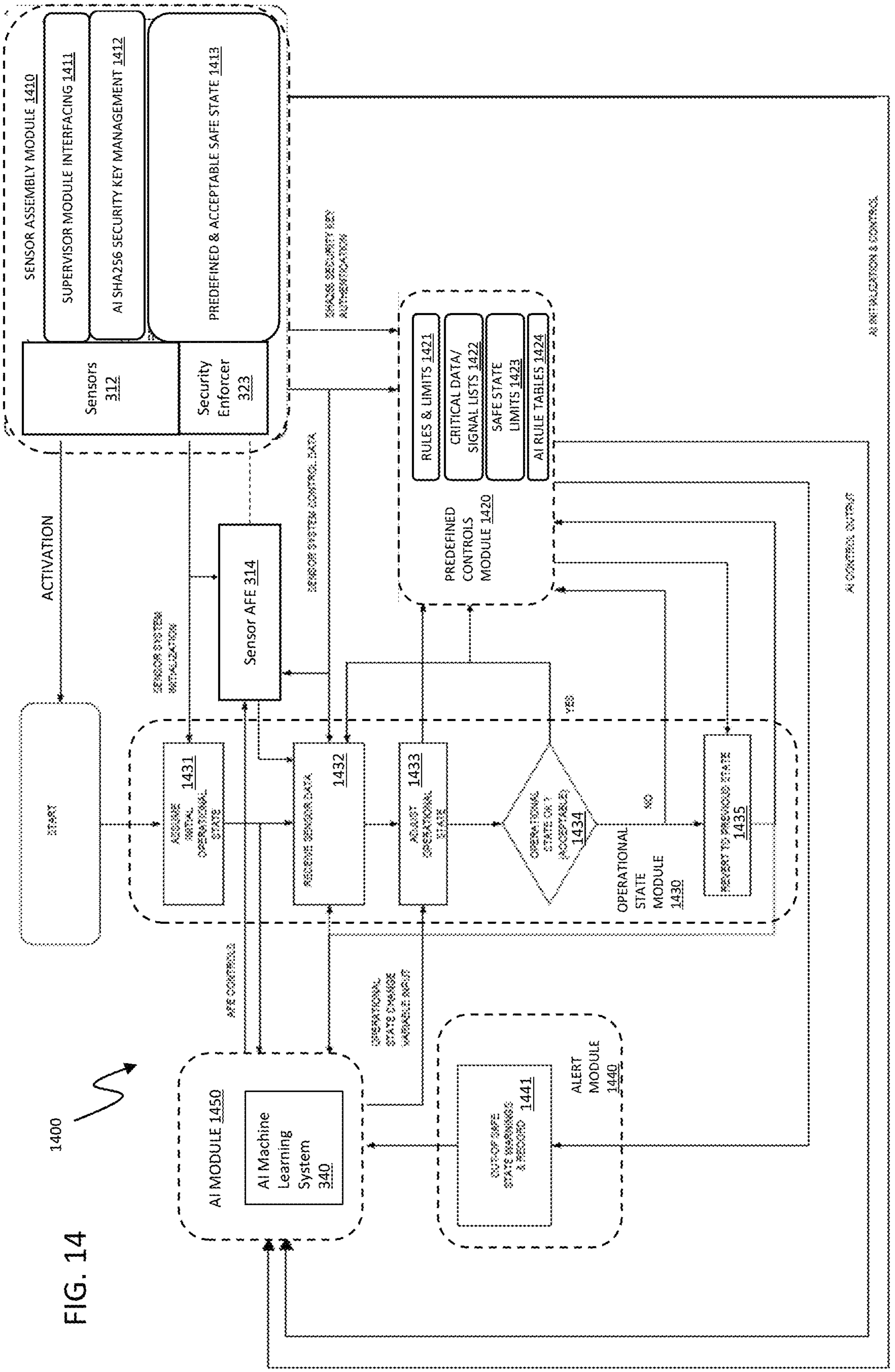
FIG. 14 is a schematic diagram illustrating information flow and interaction between different components and modules of a wearable sensor platform.

FIG. 14 is a schematic diagram 1400 illustrating an example of information flow and process interactions between different components and representative functional modules of a wearable sensor platform as described herein. As illustrated by way of example, the information and interaction exchanges are shown schematically with respect to components of the wearable sensor platform 304 discussed in connection with FIG. 3A, including the sensors 312, security enforcer 323, the sensor AFE 314, and the AI machine learning system 340, and in connection with representations of operations of functional modules, such as a sensor assembly module 1410, a pre-defined controls module 1420, an operational state module 1430, an alert module 1440 and an AI module 1450. It is noted that components of the wearable sensor platform 304 other than that shown in this figure may be used in connection with the described operations and functions of the functional modules, and the components of the wearable sensor platform 304 may perform multiple operations and functions both as part of and in addition to the operations of the described functional modules.

The sensor assembly module 1410 is illustrated schematically in connection with components such as the sensors 312, the security enforcer 323 and the sensor AFE 314, and information and data outputs from those components. The sensor assembly module 1410 further includes representations of functional operations for supervisor module interfacing 1411 (e.g. with the supervisor module 904), AI SHA256 security key management 1412, and predefined & acceptable safe state 1413. The predefined & acceptable safe state 1413 may include processing corresponding to information and configurations for initial operational state, power up state, reset state, configuration state and data acquisition synchronization & initial state of the wearable sensor platform 304.

As constrained by the supervisor module and management using the security key management techniques discussed herein, the predefined controls module 1420 provides operational information and functions that include conditions and processing for rules & limits 1421, critical data/signal lists 1422, acceptable safe state limits 1423 and AI rule tables 1424. Decisions and processes for operational states of the wearable sensor platform 304 are shown in connection with functions of the operational state module 1430, including assuming an initial operational state (block 1431) after activation of the system and sensor system initialization, and receiving sensor data (block 1432). As a result of functioning of the AI module 1450, input to the operational state module 1430 provides for adjusting the operational state (block 1433), determining whether the current operational state is acceptable (block 1434), and determining whether it is necessary to revert to a previous state (block 1435). Alerts or alarms are generated in connection with functioning of the alert module 1440, and which may include generating and/or displaying out-of-state warnings and records 1441.

Functioning of the AI module 1450, using inputs such as received AI control inputs, authorization, and sensor data measured and transmitted by the sensors 312, is enabled by the use of the AI and machine learning algorithms of the AI machine learning system 340 discussed herein. The AI module 1450 functions enable the generating of information and outputs used to adjust on an on-going or continuous basis controls and operational states of the wearable sensor platform 304. The schematically illustrated information flow and interactions between the components and representative functional modules of the wearable sensor platform 304 provide for the secure AI enabled operational adjustment of the wearable sensor platform 304 in connection with that described in detail herein.

Figure 15:
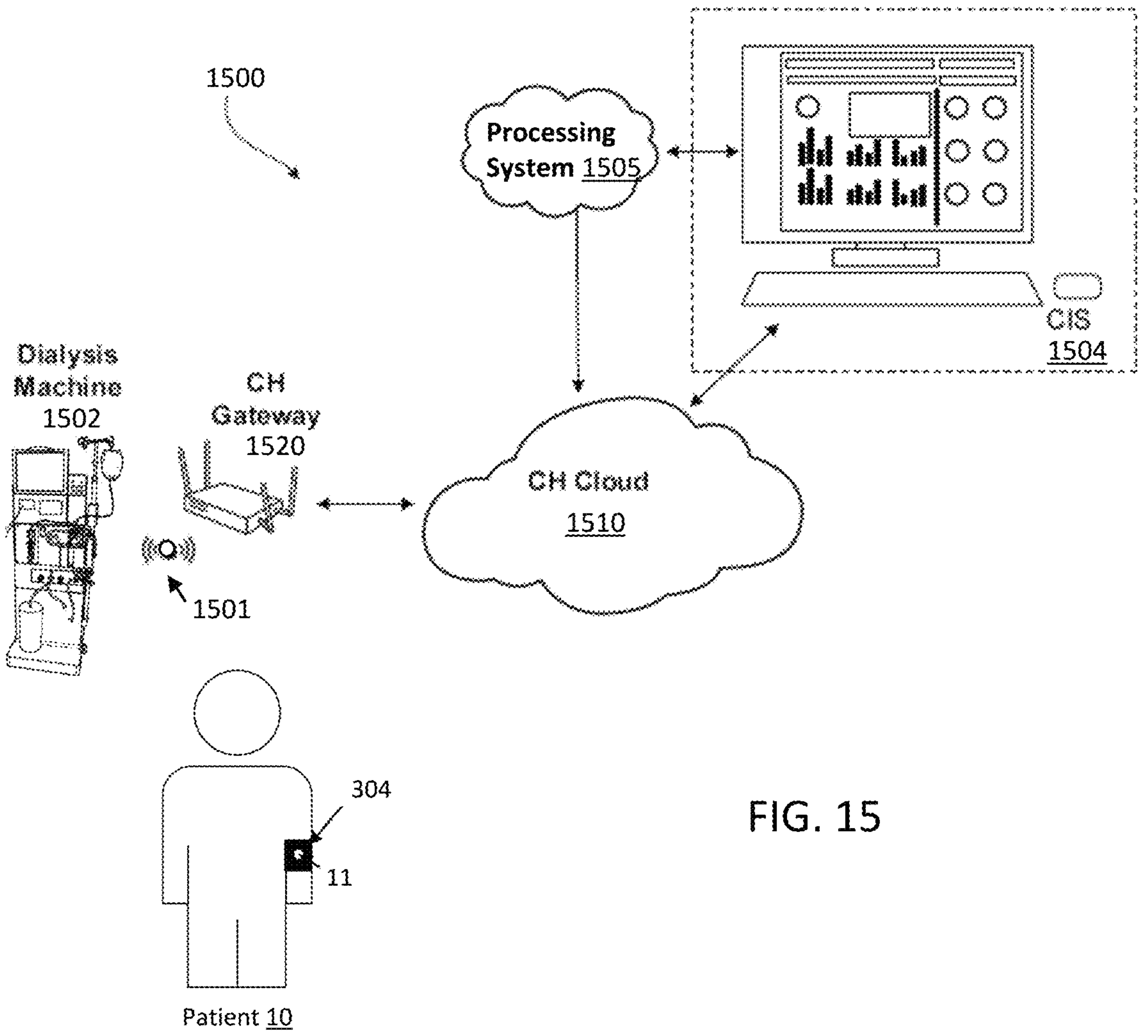
FIG. 15 is a schematic diagram showing an example of a connected medical information distribution system, for example, a connected health (CH) system, that may that may be used in connection with network aspects of the wearable sensor platform described herein.

FIG. 15 is a schematic illustration showing an example of a connected medical system, for example, a connected health (CH) system 1500, that may be used in connection with network aspects of the wearable sensor platform 304 described herein. The CH system 1500 may include, among other things, a processing system 1505, a CH cloud 1510 and a gateway (CH Gateway) 1520. The processing system 1505 may be a server and/or cloud-based system that processes, compatibility checks and/or formats medical information, including prescription information generated at a clinical information system (CIS) 1504 of a clinic or hospital, in connection with data transmission operations of the CH system 1500. The CH system 1500 may include appropriate encryption and data security mechanisms, like that discussed herein. The CH cloud 1510 may be a cloud-based application or system that serves as a communication pipeline (e.g., facilitates the transfer of data) among components of the CH system 1500 via connections to a network, the Internet.

The gateway 1520 may serve as a communication device facilitating communication among components of the CH system 1500 and other components. In various embodiments, the gateway 1520 is in communication with a dialysis machine 1502, such as a home hemodialysis machine, via a wireless connection 1501, such as a Bluetooth, Wi-Fi and/or other appropriate type of local or short-range wireless connection. The gateway 1520 may also be in connection with the CH cloud service 1510 via a secure network (e.g. Internet) connection. The gateway 1520 is configured to transmit/receive data to/from the CH cloud 1510 and transmit/receive data to/from the dialysis machine 1502. The gateway 1520 may also facilitate communication between peripheral devices, such as a smartphone and/or the wearable sensor platform 304 that may be worn by a patient 10, for example, as worn like one of more of the sleeves implementations discussed in connection with wearable sensor platforms 500, 600, 700, 800 discussed herein.

In an embodiment, during dialysis, e.g. hemodialysis, the dialysis machine 1502 interfaces with the patient 10 at a dialysis access point 11 (e.g., AVF). The dialysis machine 1502 extracts blood from the patient via a blood extraction needle, filters the blood, and reintroduces the blood to the patient via a blood injection needle. That is, during dialysis, the dialysis machine 1502 pumps blood out of the patient via the blood extraction needle, and using tubing, provides the blood to a dialyzer where the blood is filtered. The dialysis machine 1502 then circulates the blood via tubing to the blood injection needle for reintroduction to the patient.

As the patient 10 is undergoing dialysis, the wearable sensor platform 304, using the AI control features and techniques discussed herein, measures conditions of the patient, for example, conditions proximate to the access point 11 and generates sensor data. The wearable sensor platform 304 provides the sensor data and other information to the gateway 1520. The dialysis machine 1502, connected to the gateway 1520 via the wireless connection 1501, also provides treatment information to the gateway 1520. Treatment information can include blood pump rate, dialysate pump rate, type of dialysate used, treatment start time, treatment time elapsed, measured hematocrit, and so on.

The gateway 1520 can receive the data from the wearable sensor platform 304 and from the dialysis machine 1502. In some implementations, the gateway 1520 can provide the sensor data to the dialysis machine 1502 and/or can provide the treatment information and the sensor data to the CH cloud 1510 for further processing and analysis at a remote location, such as the CIS 1504. The gateway 1520 can also receive patient electronic records and prescription information from the CH cloud 1510 and that may be further transmitted, processed and used in connection with operation of the dialysis machine 1502 and/or the wearable sensor platform 304.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), magnetoresistive random access memory (MRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component (for example, as a data server), or that includes a middleware component (for example, an application server). The components of the system can be interconnected by wireless digital data communication (or a combination of data communication) in a communication network. Examples of communication networks include a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure.

What is claimed is:

1. A sensor system for monitoring a vascular access point of a subject, wherein the sensor system comprises:

a plurality of sensors configured to capture sensor data characterizing a physiological state of the subject in a vicinity of the vascular access point of the subject;

one or more computer processors; and one or more storage devices communicatively coupled to the one or more computer processors, wherein the one or more storage devices store instructions that, when executed by the one or more computer processors, cause the one or more computer processors to perform operations comprising:

continuously receiving, by one or more machine learning models, input data comprising measurements captured by the plurality of sensors of the sensor system;

continuously processing, by the one or more machine learning models, the input data in accordance with trained values of a set of model parameters of the one or more machine learning models that have been determined by a machine learning training technique to generate a set of adaptive optimizations for operational parameters of the plurality of sensors;

continuously adjusting the operational parameters of the plurality of sensors using the set of adaptive optimizations generated by the one or more machine learning models to optimize the operational parameters of the plurality of sensors with reference to an objective function, comprising managing power consumption by the plurality of sensors by performing steps comprising:

classifying, using the one or more machine learning models, a state of the vascular access point at a first time point as being an abnormal state and, in response, increasing a sampling rate of one or more of the sensors for at least a first threshold duration of time; and classifying, using the one or more machine learning models, a state of the vascular access point at a second time point as being a normal state and, in response, decreasing the sampling rate of one or more of the sensors for at least a second threshold duration of time;

after each adjustment of the operational parameters of the plurality of sensors, operating the plurality of sensors in accordance with the operational parameters that have been adaptively optimized using the one or more machine learning models; and while operating the plurality of sensors in accordance with the operational parameters that have been adaptively optimized using the one or more machine learning models:

repetitively receiving sensor data captured by the plurality of sensors, wherein the plurality of sensors captured the sensor data when operating in accordance with operational parameters that have been adaptively optimized using the one or more machine learning models;

processing the sensor data that is repetitively received from the plurality of sensors to generate a prediction characterizing a health of the vascular access point of the subject; and generating an alert based on the prediction characterizing the health of the vascular access point of the subject.

2. The sensor system of claim 1, wherein adjusting the operational parameters of the plurality of sensors using the set of adaptive optimizations generated by the one or more machine learning models comprises:

processing one or more model inputs, by the one or more machine learning models, to generate one or more machine learning model outputs that define an update to values of the operational parameters of the plurality of sensors; and adjusting the values of the operational parameters of the plurality of sensors based on the one or more machine learning model outputs.

3. The system of claim 2, wherein adjusting the values of the operational parameters of the plurality of sensors based on the one or more machine learning model outputs comprises:

determining updated values of the operational parameters of the plurality of sensors based on the one or more machine learning model outputs; and determining that the updated values of the operational parameters of the plurality of sensors are consistent with one or more constraints on the values of the operational parameters of the plurality of sensors.

4. The system of claim 1, wherein for one or more of the plurality of sensors, adjusting the operational parameters of the sensor comprises:

adjusting an ultrafiltration parameter of the sensor.

5. The system of claim 1, wherein for one or more of the plurality of sensors, adjusting the operational parameters of the sensor comprises:

adjusting a calibration parameter of the sensor.

6. The system of claim 1, wherein the objective function is dependent on at least power usage by the plurality of sensors.

7. The system of claim 1, wherein the objective function is dependent on at least on signal-to-noise ratio (SNR) of sensor data generated by the plurality of sensors.

8. The system of claim 1, wherein the objective function is dependent on at least sensor performance of the plurality of sensors.

9. The system of claim 1, wherein the operations further comprise showing the alert on a display.

10. The system of claim 1, wherein the one or more machine learning models comprise one or more neural networks models.

11. The system of claim 1, wherein the sensor system is a wearable system.

12. The system of claim 1, wherein processing the sensor data that is repetitively received from the plurality of sensors to generate a prediction characterizing a health of the vascular access point of the subject comprises conditioning the sensor data that is repetitively received from the plurality of sensors, the conditioning comprising, for each of the plurality of sensors:

processing raw sensor data repetitively received from the sensor using a conditioning machine learning model corresponding to the sensor, in accordance with trained values of a set of conditioning machine learning model parameters, to generate a set of conditioning parameters; and applying a conditioning operation, parameterized by the set of conditioning parameters generated by the conditioning machine learning model corresponding to the sensor, to the raw sensor data repetitively received from the sensor.

13. The system of claim 12, wherein for each sensor of the plurality of sensors, the trained values of the set of conditioning machine learning model parameters corresponding to the sensor are subject-specific values that are determined through training, by a machine learning training technique, on subject-specific raw sensor data characterizing the physiological state of the subject.

14. The system of claim 1, wherein processing the sensor data that is repetitively received from the plurality of sensors to generate a prediction characterizing a health of the vascular access point of the subject comprises:

determining differential readings between pairs of sensors of the plurality of sensors; and determining whether the differential readings satisfy a threshold.

15. The system of claim 1, wherein generating a prediction characterizing a health of the vascular access point of the subject comprises:

classifying whether the vascular access point is infected.

16. The system of claim 1, wherein generating a prediction characterizing a health of the vascular access point of the subject comprises:

classifying an optimal transfer rate through the vascular access point.

17. A method of using a sensor system to monitor a vascular access point of a subject, wherein the sensor system comprises a plurality of sensors configured to capture sensor data characterizing a physiological state of the subject in a vicinity of the vascular access point of the subject, the method comprising:

continuously receiving, by one or more machine learning models, input data comprising measurements captured by the plurality of sensors of the sensor system;

continuously processing, by the one or more machine learning models, the input data in accordance with trained values of a set of model parameters of the one or more machine learning models that have been determined by a machine learning training technique to generate a set of adaptive optimizations for operational parameters of the plurality of sensors;

continuously adjusting the operational parameters of the plurality of sensors using the set of adaptive optimizations generated by the one or more machine learning models to optimize the operational parameters of the plurality of sensors with reference to an objective function, comprising managing power consumption by the plurality of sensors by performing steps comprising:

classifying, using the one or more machine learning models, a state of the vascular access point at a first time point as being an abnormal state and, in response, increasing a sampling rate of one or more of the sensors for at least a first threshold duration of time; and classifying, using the one or more machine learning models, a state of the vascular access point at a second time point as being a normal state and, in response, decreasing the sampling rate of one or more of the sensors for at least a second threshold duration of time;

after each adjustment of the operational parameters of the plurality of sensors, operating the plurality of sensors in accordance with the operational parameters that have been adaptively optimized using the one or more machine learning models; and while operating the plurality of sensors in accordance with the operational parameters that have been adaptively optimized using the one or more machine learning models:

repetitively receiving sensor data captured by the plurality of sensors, wherein the plurality of sensors captured the sensor data when operating in accordance with operational parameters that have been adaptively optimized using the one or more machine learning models;

processing the sensor data that is repetitively received from the plurality of sensors to generate a prediction characterizing a health of the vascular access point of the subject; and generating an alert based on the prediction characterizing the health of the vascular access point of the subject.

18. One or more non-transitory computer storage media storing instructions that when executed by one or more computers cause the one or more computers to perform operations for using a sensor system to monitor a vascular access point of a subject, wherein the sensor system comprises a plurality of sensors configured to capture sensor data characterizing a physiological state of the subject in a vicinity of the vascular access point of the subject, the operations comprising:

continuously receiving, by one or more machine learning models, input data comprising measurements captured by the plurality of sensors of the sensor system;

continuously processing, by the one or more machine learning models, the input data in accordance with trained values of a set of model parameters of the one or more machine learning models that have been determined by a machine learning training technique to generate a set of adaptive optimizations for operational parameters of the plurality of sensors;

continuously adjusting the operational parameters of the plurality of sensors using the set of adaptive optimizations generated by the one or more machine learning models to optimize the operational parameters of the plurality of sensors with reference to an objective function, comprising managing power consumption by the plurality of sensors by performing steps comprising:

classifying, using the one or more machine learning models, a state of the vascular access point at a first time point as being an abnormal state and, in response, increasing a sampling rate of one or more of the sensors for at least a first threshold duration of time; and classifying, using the one or more machine learning models, a state of the vascular access point at a second time point as being a normal state and, in response, decreasing the sampling rate of one or more of the sensors for at least a second threshold duration of time;

after each adjustment of the operational parameters of the plurality of sensors, operating the plurality of sensors in accordance with the operational parameters that have been adaptively optimized using the one or more machine learning models; and while operating the plurality of sensors in accordance with the operational parameters that have been adaptively optimized using the one or more machine learning models:

repetitively receiving sensor data captured by the plurality of sensors, wherein the plurality of sensors captured the sensor data when operating in accordance with operational parameters that have been adaptively optimized using the one or more machine learning models;

processing the sensor data that is repetitively received from the plurality of sensors to generate a prediction characterizing a health of the vascular access point of the subject; and generating an alert based on the prediction characterizing the health classification of the state of the vascular access point of the subject.

19. The non-transitory computer storage media of claim 18, wherein adjusting the operational parameters of the plurality of sensors using the set of adaptive optimizations generated by the one or more machine learning models comprises:

processing one or more model inputs, by the one or more machine learning models, to generate one or more machine learning model outputs that define an update to values of the operational parameters of the plurality of sensors; and adjusting the values of the operational parameters of the plurality of sensors based on the one or more machine learning model outputs.

20. The non-transitory computer storage media of claim 19, wherein adjusting the values of the operational parameters of the plurality of sensors based on the one or more machine learning model outputs comprises:

determining updated values of the operational parameters of the plurality of sensors based on the one or more machine learning model outputs; and determining that the updated values of the operational parameters of the plurality of sensors are consistent with one or more constraints on the values of the operational parameters of the plurality of sensors.

* * * * *